US008460858B2

(12) United States Patent
Maeda et al.

(10) Patent No.: US 8,460,858 B2
(45) Date of Patent: Jun. 11, 2013

(54) NEAR-INFRARED-RAY ABSORBING MATERIAL CONTAINING CYANINE COMPOUND, AND CYANINE COMPOUND

(75) Inventors: Yosuke Maeda, Tokyo (JP); Ryoya Otsuki, Tokyo (JP); Koichi Shigeno, Tokyo (JP)

(73) Assignee: Adeka Corporation, Tokyo (JP)

( * ) Notice: Subject to any disclaimer, the term of this patent is extended or adjusted under 35 U.S.C. 154(b) by 169 days.

(21) Appl. No.: 13/129,692

(22) PCT Filed: Nov. 18, 2009

(86) PCT No.: PCT/JP2009/069574
§ 371 (c)(1),
(2), (4) Date: May 17, 2011

(87) PCT Pub. No.: WO2010/073857
PCT Pub. Date: Jul. 1, 2010

(65) Prior Publication Data
US 2011/0224334 A1 Sep. 15, 2011

(30) Foreign Application Priority Data

Dec. 25, 2008 (JP) ................. 2008-329102
Feb. 12, 2009 (JP) ................. 2009-030004

(51) Int. Cl.
*C07D 209/10* (2006.01)
*G03C 1/40* (2006.01)

(52) U.S. Cl.
USPC ........... 430/522; 430/584; 430/594; 430/595; 548/488

(58) Field of Classification Search
USPC .......................................... 548/455; 430/522
See application file for complete search history.

(56) References Cited

U.S. PATENT DOCUMENTS

| 5,541,235 | A | 7/1996 | Busman et al. |
| 5,783,377 | A | 7/1998 | Mee et al. |
| 7,524,619 | B2 | 4/2009 | Yamanobe et al. |
| 2005/0040378 | A1 | 2/2005 | Kobayashi et al. |
| 2008/0131166 | A1 | 6/2008 | Yokoyama et al. |

FOREIGN PATENT DOCUMENTS

| CN | 1714126 | 12/2005 |
| EP | 1 772 282 | 4/2007 |
| EP | 2 003 171 | 12/2008 |
| JP | 8-253705 | 10/1996 |
| JP | 8-295821 | 11/1996 |
| JP | 10-152620 | 6/1998 |
| JP | 2005099755 | 4/2005 |
| JP | 2005325292 | 11/2005 |
| JP | 2006282646 | 10/2006 |
| JP | 2007-326350 | 12/2007 |
| JP | 2008-100451 | 5/2008 |
| JP | 2008-120074 | 5/2008 |
| JP | 2008-274230 | 11/2008 |

OTHER PUBLICATIONS

European Search Report—PCT/JP2009/069574—Sep. 3, 2012.

A.A. Ishchenko—"The length of the polymethine chain and the spectral-luminescent properties of symmetrical dyes", Russian Chemical Bulletin, vol. 43, No. 7, Jul. 7, 1994, pp. 1161-1174, XP002681912.
International Search Report, PCT/JP2009/069574, Dec. 15, 2009.
Chinese Office Action dated Jan. 4, 2013 in corresponding Chinese Patent Application No. 200980146364.8 with English translation of Chinese Office Action.

*Primary Examiner* — Shawquia Young
(74) *Attorney, Agent, or Firm* — Young & Thompson

(57) ABSTRACT

A near-infrared-ray absorbing material containing a cyanine compound per formula (I) exhibits a sharp light absorption in wavelength range 800-1000 nm, with excellent light resistance. $R^1$ - $R^4$, $Y^1$, $Y^2$ represents hydrogen atom, a group of formula (II) or (II'), etc., and $An^{q-}$ represents a q-valent anion, provided that at least $R^1$ is a group of formula (II) or (II') or $An^{q-}$ is an ion of formula (III); $R^{11}$ - $R^{13}$ each represents a hydrogen atom, hydroxyl group, etc.; $Z^1$, $Z^2$ represents a $C_{1-10}$ alkyl group, etc. In formula (II'), the bond between G' and T' is a double bond or a conjugated double bond; G' represents a carbon atom; T' represents a carbon atom or a nitrogen atom; the ring including G' and T' represents a 6-membered ring, etc.; w' is 0-4; and $R^{01'}$ represents a hydrogen atom, hydroxy, etc. In formula (III), $R^5$ and $R^6$ represents a halogen-substituted $C_{1-8}$ alkyl group.

(I)

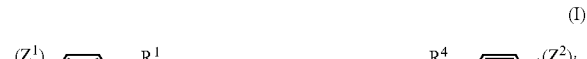

(II)

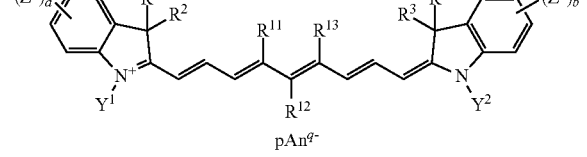

(II')

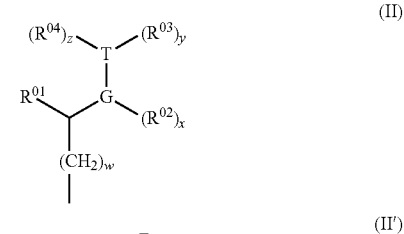

(III)

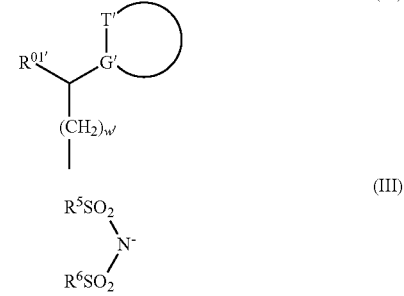

20 Claims, No Drawings

NEAR-INFRARED-RAY ABSORBING MATERIAL CONTAINING CYANINE COMPOUND, AND CYANINE COMPOUND

TECHNICAL FIELD

The present invention relates to a near-infrared-ray absorbing material containing a cyanine compound, and a novel cyanine compound having a specific structure. The near-infrared-ray absorbing material is suitable for optical filters for image display devices and resin compositions for laser welding. The cyanine compound is useful as optical elements such as light absorbers, optical recording agents, and optical sensitizers.

BACKGROUND ART

Compounds having strong light absorption at specific wavelengths are used as optical elements in optical filters for image display devices such as liquid crystal displays (LCDs), plasma display panels (PDPs), electroluminescence displays (ELDs), cathode-ray tube displays (CRTs), fluorescent display tubes, and field emission displays, and in optical recording layers of optical recording media such as DVD±Rs.

Such compounds are used e.g. as light absorbers when employed as optical elements in optical filters for image display devices. Image display devices create color images by combining light in the three primary colors, red, blue, and green, but the beams used for creating the color images include light that impairs display quality, such as 550- to 620-nm light between green and red, and also include 750- to 1100-nm light that possibly causes malfunction of infrared remote controllers. Thus, optical filters are required to have a function of selectively absorbing light in such unwanted wavelengths, and also a function of absorbing light ranging from 480 to 500 nm and from 540 to 560 nm in order to prevent reflection and glare of external light from fluorescent lamps etc. In image display devices and the like, therefore, optical filters containing light-absorbing compounds (light absorbers) that selectively absorb light at such wavelengths are used.

In recent years, there has also been a demand for light absorbers that can selectively absorb near-infrared rays particularly ranging from 800 to 1000 nm in order to provide display elements with sufficient color purity and color separation and thus achieve high image quality. Near-infrared-ray absorbing materials containing such light absorbers are widely used for optical filters as well as for other materials, such as photosensitive materials for laser welding, laser blocking materials, and heat-ray blocking materials. These near-infrared-ray absorbing materials used in such applications are expected to absorb light only within the targeted range—i.e., have a narrow half-width at $\lambda_{max}$ and an extremely sharp light absorption—and also have the ability to maintain their functionalities even when subjected to light and/or heat, for example.

Various optical filters containing light absorbers are known. For example, Patent Document 1 discloses a near-infrared-ray absorbing film having a near-infrared-ray absorbing layer containing, as essential components, a cyanine compound and a diimmonium compound having specific structures. Patent Document 2 discloses a near-infrared-ray absorbing optical filter containing a metal complex having a specific structure. Patent Document 3 discloses a near-infrared-ray blocking filter containing a diimmonium salt. Patent Documents 4 and 5 disclose cyanine compounds having an absorption maximum near 900 nm. The compounds used for these near-infrared-ray absorbing films and filters, however, have insufficient performance: for example, the absorptivity exhibits poor light resistance in the range between 800 and 1000 nm, and the absorption is large in the visible region.

Patent Document 6 discloses an optical recording material containing a cyanine compound having a specific group. The document, however, contains no concrete disclosure on compounds having an absorption maximum in the range between 800 and 1000 nm, nor does it teach anything about using the disclosed compound as a near-infrared-ray absorbing material.

Further, Patent Document 7 discloses the use of a phthalocyanine compound as a near-infrared-ray absorbing material for laser welding of plastics. To absorb laser beams with higher efficiency, however, colorant compounds with a higher $\epsilon$ are desirable.

CITATION LIST

Patent Documents

Patent Document 1: US 2005/040378 A1

Patent Document 2: JP-A-2005-99755

Patent Document 3: JP-A-2005-325292

Patent Document 4: JP-A-8-295821

Patent Document 5: US 2008/131166 A1

Patent Document 6: JP-A-2008-100451

Patent Document 7: JP-A-2006-282646

SUMMARY OF INVENTION

Technical Problem

An object of the present invention is to provide a near-infrared-ray absorbing material exhibiting a sharp light absorption in a wavelength range between 800 and 1000 nm, having excellent light resistance, and suitable particularly for optical filters for image display devices and resin compositions for laser welding; an optical filter and a resin composition for laser welding containing the above near-infrared-ray absorbing material; and a novel cyanine compound useful as an optical element.

Solution to Problem

Inventors have made diligent research to find that a near-infrared-ray absorbing material containing a cyanine compound having a specific molecular structure exhibits a sharp light absorption in a specific wavelength range, can dramatically improve the imaging properties of image display devices compared to other near-infrared-ray absorbing materials containing conventional cyanine compounds, and is also excellent in light resistance.

The present invention has been made based on the above finding and provides a near-infrared-ray absorbing material containing at least one cyanine compound represented by general formula (I) shown below:

[Chem. 1]

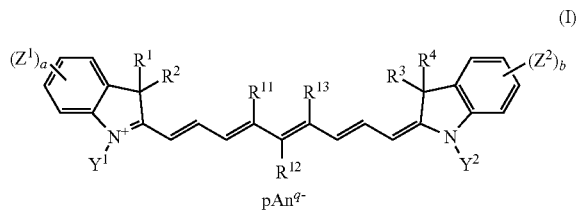

wherein: $R^1$, $R^2$, $R^3$, $R^4$, $Y^1$, and $Y^2$ each independently represent a hydrogen atom, a group represented by general formula (II) or general formula (II') shown below, a $C_{1-20}$ alkyl group, a $C_{6-30}$ aryl group, or a $C_{7-30}$ arylalkyl group, an alkylene moiety of the alkyl group or the arylalkyl group being optionally interrupted by —O— or —S—; $R^1$ and $R^2$, as well as $R^3$ and $R^4$, may independently be connected with each other to form a 3- to 6-membered alicyclic group;

$An^{q-}$ represents a q-valent anion; q is an integer of 1 or 2; p represents a coefficient for keeping the electrical charge neutral;

with the proviso that at least either $R^1$ is a group represented by the general formula (II) or (II'), or the anion represented by $An^{q-}$ is an ion represented by general formula (III) shown below;

$R^{11}$, $R^{12}$, and $R^{13}$ each independently represent a hydrogen atom, a hydroxyl group, a halogen atom, a cyano group, a diphenylamino group, a $C_{1-20}$ alkyl group, a $C_{6-30}$ aryl group, or a $C_{7-30}$ arylalkyl group, an alkylene moiety of the alkyl group or the arylalkyl group being optionally interrupted by —O— or —S—; $R^{11}$ and $R^{13}$ may be connected to each other to form a 4- to 8-membered cycloalkene ring, a methylene moiety of the formed cycloalkene ring being optionally substituted by a hydroxyl group, a halogen atom, a cyano group, a $C_{6-30}$ aryl group, a diphenylamino group, a $C_{1-8}$ alkyl group, or a $C_{1-8}$ alkoxy group;

$Z^1$ and $Z^2$ each independently represent a $C_{1-10}$ alkyl group, a $C_{6-20}$ aryl group, a $C_{7-20}$ arylalkyl group, a nitro group, a cyano group, a hydroxyl group, a carboxyl group, or a halogen atom, or a plurality of the $Z^1$ groups, or a plurality of the $Z^2$ groups, may be bonded together to form a ring structure; a hydrogen atom in $Z^1$ and $Z^2$ may optionally be substituted by a nitro group, a cyano group, a hydroxyl group, a carboxyl group, or a halogen atom; a methylene group in $Z^1$ and $Z^2$ may optionally be interrupted by —O—, —CO—, —OCO—, or —COO—; and a and b each independently represent an integer of 0 to 4;

[Chem. 2A]

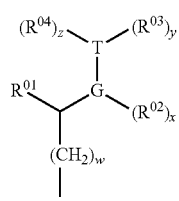

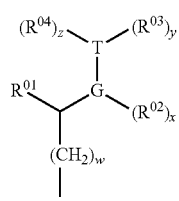

in the above general formula (II): the bond between G and T is a double bond, a conjugated double bond, or a triple bond; G represents a carbon atom; T represents a carbon atom, an oxygen atom, or a nitrogen atom; w represents a number from 0 to 4; x, y, and z each represent 0 or 1 (if T is an oxygen atom, then y and z are 0; if T is a nitrogen atom, then y+z is 0 or 1); $R^{01}$, $R^{02}$, $R^{03}$, and $R^{04}$ each independently represent a hydrogen atom, a hydroxyl group, a nitro group, a cyano group, a halogen atom, or a $C_{1-4}$ alkyl group that may optionally have a substituent, a methylene group in the alkyl group being optionally replaced by —O— or —CO—; and $R^{01}$ and $R^{04}$ may be bonded to form a cycloalkene ring or a heterocycle;

in the above general formula (II'): the bond between G' and T' is a double bond or a conjugated double bond; G' represents a carbon atom; T' represents a carbon atom or a nitrogen atom; the ring containing G' and T' represents a 5-membered ring that may contain a hetero atom, a 6-membered ring that may contain a hetero atom, a naphthalene ring, a quinoline ring, an isoquinoline ring, an anthracene ring, or an anthraquinone ring; the ring containing G' and T' may optionally be substituted by a halogen atom, a hydroxyl group, a nitro group, a cyano group, a $C_{1-4}$ alkyl group, or a $C_{1-4}$ alkoxy group; w' represents a number from 0 to 4; and $R^{01'}$ represents a hydrogen atom, a hydroxyl group, a nitro group, a cyano group, a halogen atom, or a $C_{1-4}$ alkyl group that may optionally have a substituent, a methylene group in the alkyl group being optionally replaced by —O— or —CO—;

[Chem. 2B]

wherein, $R^5$ and $R^6$ each independently represent a halogen-substituted $C_{1-8}$ alkyl group.

The invention also provides a film-forming composition containing the above near-infrared-ray absorbing material and an optical filter made using the film-forming composition.

The invention also provides a resin composition for laser welding, containing the above near-infrared-ray absorbing material.

The invention also provides a cyanine compound wherein $R^1$ in the general formula (I) is a group represented by the general formula (II) or (II').

ADVANTAGEOUS EFFECTS OF INVENTION

The near-infrared-ray absorbing material containing the cyanine compound represented by the general formula (I) exhibits a sharp light absorption in the range between 800 and 1000 nm and especially between 850 and 950 nm, can suitably be used as optical filters for image display applications and especially for plasma display applications, and is also useful for resin compositions for laser welding. The cyanine compound of the invention is useful as an optical element, such as a light absorber, and is superior in light resistance to conventional cyanine compounds.

Description of Embodiments

The near-infrared-ray absorbing material of the present invention, and cyanine compounds suitable for the near-infrared-ray absorbing material, as well as film-forming compositions, optical filters, and resin compositions for laser welding, will be described in detail below according to preferred embodiments thereof.

First, the near-infrared-ray absorbing material of the invention and cyanine compounds suitable for the near-infrared-ray absorbing material will be described in detail.

The near-infrared-ray absorbing material of the invention contains at least one cyanine compound represented by the general formula (I). In the general formula (I) of the cyanine compound, at least either $R^1$ is a group represented by the general formula (II) or (II'), or the anion represented by $An^{q-}$ is an ion represented by the general formula (III).

Examples of the $C_{1-20}$ alkyl group represented by $R^1$, $R^2$, $R^3$, $R^4$, $Y^1$, and $Y^2$ in the general formula (I) include methyl, ethyl, propyl, isopropyl, butyl, s-butyl, t-butyl, isobutyl, amyl, isoamyl, t-amyl, hexyl, cyclohexyl, cyclohexylmethyl, 2-cyclohexylethyl, heptyl, isoheptyl, t-heptyl, n-octyl, isooctyl, t-octyl, 2-ethylhexyl, nonyl, isononyl, decyl, dodecyl, tridecyl, tetradecyl, pentadecyl, hexadecyl, heptadecyl, octadecyl, 2-methoxyethyl, 3-methoxypropyl, 4-methoxybutyl, 2-butoxyethyl, methoxyethoxyethyl, methoxyethoxyethoxyethyl, 3-methoxybutyl, and 2-methylthioethyl. Examples of the $C_{6-30}$ aryl group include phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-t-butylphenyl, 4-hexylphenyl, 4-cyclohexylphenyl, 4-octylphenyl, 4-(2-ethylhexyl)phenyl, 4-stearylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-t-butylphenyl, cyclohexylphenyl, 2-phenoxyethyl, and 2-phenylthioethyl. Examples of the $C_{7-30}$ arylalkyl group include benzyl, phenethyl, 2-phenylpropan-2-yl, diphenylmethyl, triphenylmethyl, styryl, and cinnamyl. Preferred among the above are $C_{1-10}$ alkyl groups.

$R^1$ and $R^2$, as well as $R^3$ and $R^4$, may independently be connected with each other to form a 3- to 6-membered alicyclic group. Examples of the 3- to 6-membered alicyclic group include cyclopropane-1,1-diyl, cyclobutane-1,1-diyl, 2,4-dimethylcyclobutane-1,1-diyl, 3-dimethylcyclobutane-1,1-diyl, cyclopentane-1,1-diyl, cyclohexane-1,1-diyl, tetrahydropyran-4,4-diyl, thiane-4,4-diyl, piperidine-4,4-diyl, N-substituted piperidine-4,4-diyl, morpholine-2,2-diyl, morpholine-3,3-diyl, N-substituted morpholine-2,2-diyl, and N-substituted morpholine-3,3-diyl. Examples of the N-substituents include the groups given as examples for $R^1$, $R^2$, $R^3$, $R^4$, $Y^1$, and $Y^2$ described above.

Examples of the $C_{1-20}$ alkyl group, the $C_{6-30}$ aryl group, and the $C_{7-30}$ arylalkyl group represented by $R^{11}$, $R^{12}$, and $R^{13}$ include the groups given as examples for $R^1$, $R^2$, $R^3$, $R^4$, $Y^1$, and $Y^2$ described above. The halogen atom may be fluorine, chlorine, bromine, or iodine. Examples of the 4- to 8-membered cycloalkene ring formed by connecting $R^{11}$ and $R^{13}$ include a cyclobutene ring, a cyclopentene ring, a cyclohexene ring, a cycloheptene ring, and a cyclooctene ring. In cases where $R^{11}$ and $R^{13}$ together form a cycloalkene ring, the halogen atom that may optionally substitute the methylene moiety in the ring includes fluorine, chlorine, bromine, and iodine; examples of the $C_{6-30}$ aryl group include the aryl groups given as examples for $R^2$, $R^3$, $R^4$, $Y^1$, and $Y^2$ described above; examples of the $C_{1-8}$ alkyl group include the alkyl groups given as examples for $R^2$, $R^3$, $R^4$, $Y^1$, and $Y^2$ described above whose number of carbon atoms is within the defined range; and examples of the $C_{1-8}$ alkoxy group include groups wherein an oxygen atom is attached to the alkyl groups given as examples for $R^1$, $R^2$, $R^3$, $R^4$, $Y^1$, and $Y^2$ described above whose number of carbon atoms is within the defined range.

Examples of the $C_{1-10}$ alkyl group, the $C_{6-20}$ aryl group, and the $C_{7-20}$ arylalkyl group represented by $Z^1$ and $Z^2$ include the groups given as examples for $R^1$, $R^2$, $R^3$, $R^4$, $Y^1$, and $Y^2$ described above whose number of carbon atoms is within the defined range, and the halogen atom may be fluorine, chlorine, bromine, or iodine. Examples of the ring formed by bonding of a plurality of the $Z^1$ groups, or a plurality of the $Z^2$ groups, include a benzene ring, a naphthalene ring, an anthracene ring, a phenanthrene ring, a cyclohexane ring, a cyclobutane ring, a cyclopentane ring, a cyclohexene ring, a cycloheptane ring, a piperidine ring, a piperazine ring, a pyrrolidine ring, a morpholine ring, a thiomorpholine ring, a pyridine ring, a pyrazine ring, a pyrimidine ring, a pyridazine ring, a triazine ring, a quinoline ring, an isoquinoline ring, an imidazole ring, an oxazole ring, and an imidazolidine ring.

The anion represented by $An^{q-}$ in the general formula (I) may, for example, be a monovalent anion or a divalent anion. Examples of monovalent anions include: halide ions, such as chloride, bromide, iodide, and fluoride; inorganic anions, such as perchlorate, chlorate, thiocyanate, hexafluorophosphate, hexafluoroantimonate, and tetrafluoroborate; organic sulfonate anions, such as benzenesulfonate, toluenesulfonate, trifluoromethanesulfonate, diphenylamine-4-sulfonate, 2-amino-4-methyl-5-chlorobenzenesulfonate, 2-amino-5-nitrobenzenesulfonate, and N-alkyl (or aryl) diphenylamine-4-sulfonate; organic phosphate anions, such as octylphosphate, dodecylphosphate, octadecylphosphate, phenylphosphate, nonylphenylphosphate, 2,2'-methylene-bis(4,6-di-t-butylphenyl)phosphonate; ions represented by the general formula (III) (concrete examples including bis-trifluoromethylsulfonylimide ions and bis-perfluorobutanesulfonylimide ions); perfluoro-4-ethylcyclohexanesulfonate ions; tetrakis(pentafluorophenyl)borate ions; and tris(fluoroalkylsulfonyl) carbanions. Examples of divalent anions include benzenedisulfonate and naphthalenedisulfonate. It is also possible to use, for example, quencher anions having a function of de-exciting (quenching) excited active molecules, and/or metallocene anions, such as ferrocene and ruthenocene, in which an anionic group, such as a carboxyl, a phosphonate, or a sulfonate group, is present on the cyclopentadienyl ring(s). Further, the coefficient "p" is selected so that the electric charge is kept neutral within the entire molecule.

Examples of the quencher anions include anions represented by general formula (1) or (2) shown below, or anions represented by formula (3), (4), (5), (6), (7), (8), (9), (10), (11), or (12) shown below. Examples also include anions disclosed in JP-A-60-234892, JP-A-5-43814, JP-A-5-305770, JP-A-6-239028, JP-A-9-309886, JP-A-9-323478, JP-A-10-45767, JP-A-11-208118, JP-A-2000-168237, JP-A-2002-201373, JP-A-2002-206061, JP-A-2005-297407, JP-B-7-96334, and WO 98/29257.

[Chem. 3]

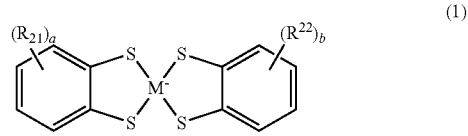

(1)

-continued

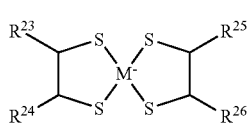
(2)

In the formula, M represents Fe, Co, Ni, Ti, Cu, Zn, Zr, Cr, Mo, Os, Mn, Ru, Sn, Pd, Rh, Pt, or Ir; $R^{21}$ and $R^{22}$ each represent a halogen atom, a $C_{1-8}$ alkyl group, a $C_{6-30}$ aryl group, or a —$SO_2$-G group; G represents an alkyl group, an aryl group that may optionally be substituted by a halogen atom, a dialkylamino group, a diarylamino group, a piperidino group, or a morpholino group; and "a" and "b" each independently represent a number of 0 to 4, $R^{23}$, $R^{24}$, $R^{25}$, and $R^{26}$ each independently represent an alkyl group, an alkylphenyl group, an alkoxyphenyl group, or a halogenated phenyl group.

[Chem. 4]

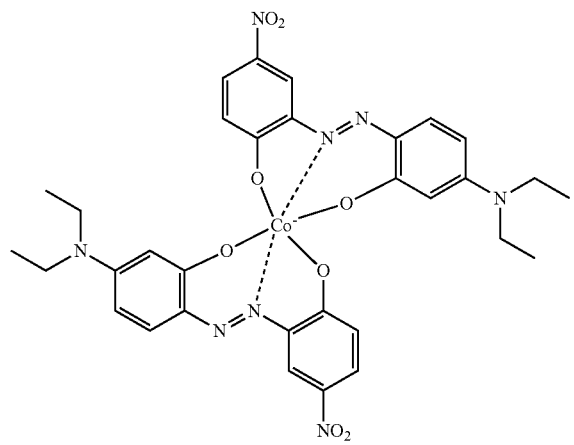
(3)

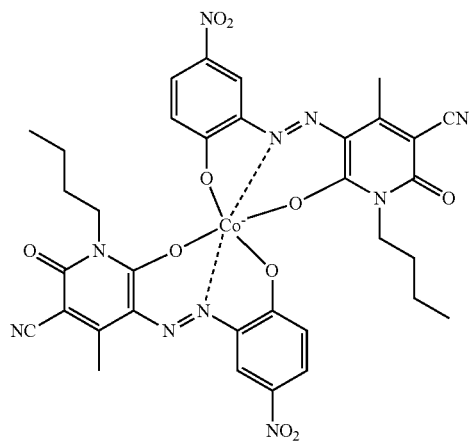
(4)

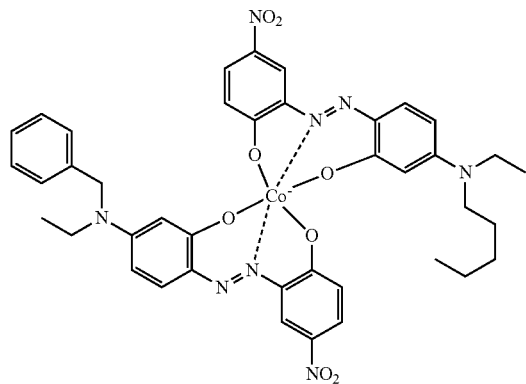
(5)

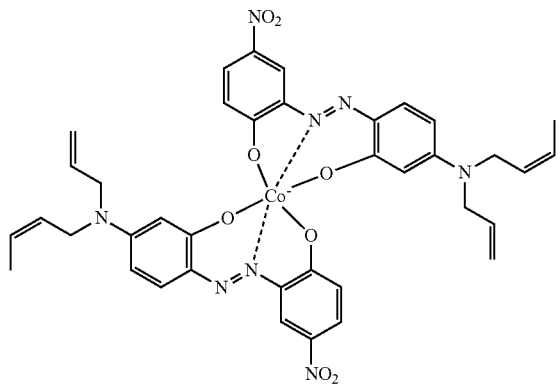
(6)

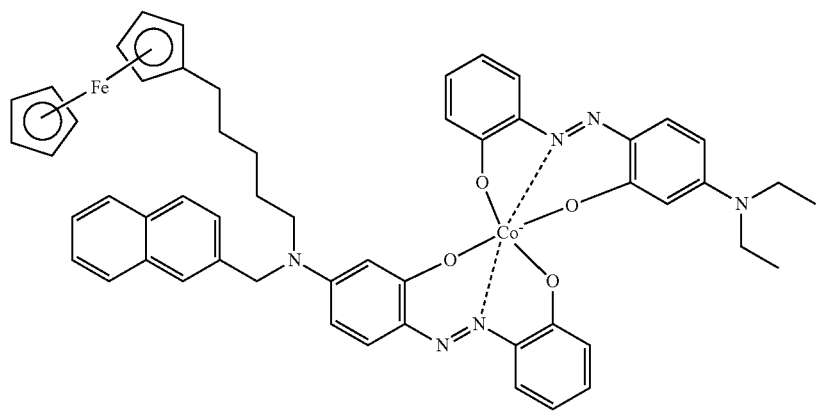
(7)

-continued

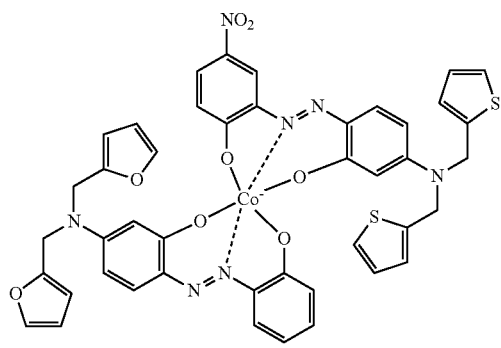
(8)

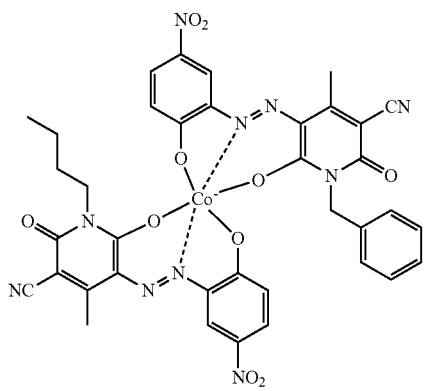
(9)

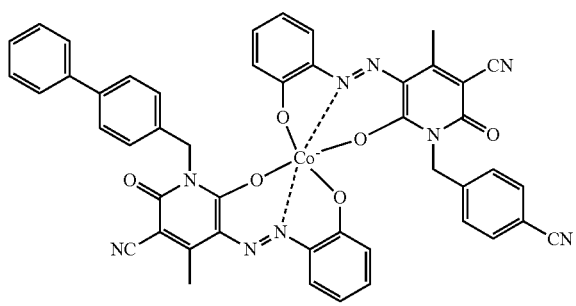
(10)

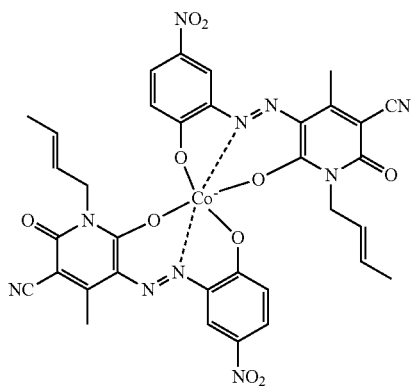
(11)

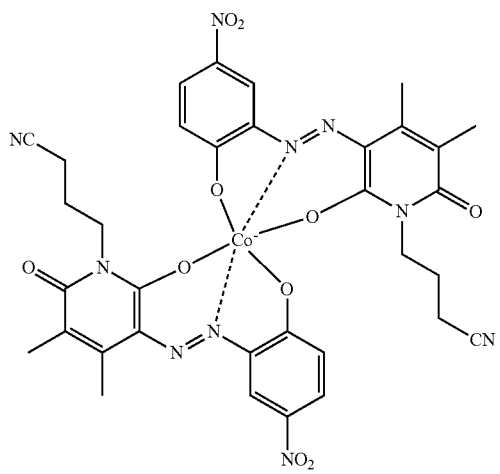
(12)

Among the various anions listed above, preferable anions represented by $An^{q-}$ are halide ions, hexafluorophosphate ions, perchlorate ions, tetrafluoroborate ions, ions represented by the general formula (III), and quencher anions represented by formulae (1) to (12) shown above. Particularly, a cyanine compound in which the anion represented by $An^{q-}$ is an ion represented by the general formula (III) is preferable because of its excellent solubility.

Examples of the halogen-substituted $C_{1-8}$ alkyl group represented by $R^5$ and $R^6$ in the general formula (III) include groups wherein the substituents given as examples of the alkyl groups represented by $R^1$, $R^2$, $R^3$, $R^4$, $Y^1$, and $Y^2$ in the general formula (I), whose number of carbon atoms is within the defined range, have been substituted by at least one halogen atom. The halogen atom may be fluorine, chlorine, bromine, or iodine, but fluorine is preferred because the solubility of the resultant cyanine compound can be improved. Concrete examples of fluorosubstituted alkyl groups substituted by at least one fluorine atom include trifluoromethyl, difluoromethyl, monofluoromethyl, pentafluoroethyl, tetrafluoroethyl, trifluoroethyl, difluoroethyl, heptafluoropropyl, hexafluoropropyl, pentafluoropropyl, tetrafluoropropyl, trifluoropropyl, and perfluorobutyl; particularly preferable among the above is trifluoromethyl.

Examples of the halogen atom represented by $R^{01}$, $R^{02}$, $R^{03}$, and $R^{04}$ in the above general formula (II) and $R^{01'}$ in the above general formula (II') include fluorine, chlorine, bromine, and iodine. Examples of the $C_{1-4}$ alkyl group represented by $R^{01}$, $R^{02}$, $R^{03}$, and $R^{04}$ in the above general formula (II) and $R^{01'}$ the above general formula (II') include methyl, ethyl, propyl, isopropyl, butyl, s-butyl, t-butyl, and isobutyl. Examples of the group in which the methylene group in the alkyl group is replaced by —O— include methoxy, ethoxy, propyloxy, isopropyloxy, methoxymethyl, ethoxymethyl, and 2-methoxyethyl. Examples of the group in which the methylene group in the alkyl group is replaced by —CO— include acetyl, 1-carbonyl ethyl, acetylmethyl, 1-carbonylpropyl, 2-oxobutyl, 2-acetylethyl, and 1-carbonylisopropyl. Any of these groups may have a substituent. Examples of the cycloalkene ring formed by connecting $R^{01}$ and $R^{04}$ include a cyclopropene ring, a cyclobutene ring, a cyclopentene ring, and a cyclohexene ring. Examples of the heterocycle formed by connecting $R^{01}$ and $R^{04}$ include a tetrahydropyran ring, a piperidine ring, a piperazine ring, a pyrrolidine ring, a morpholine ring, a thiomorpholine ring, a pyridine ring, a pyrazine ring, a pyrimidine ring, a pyridazine ring, a triazine ring, a quinoline ring, an isoquinoline ring, an imidazole ring, an oxazole ring, an imidazolidine ring, a pyrazolidine ring, an isoxazolidine ring, and an isothiazolidine ring. The ring may be fused with another ring or may be substituted. Examples of the substituent optionally present in the $C_{1-4}$ alkyl group represented by $R^{01}$, $R^{02}$, $R^{03}$, and $R^{04}$ in the above general formula (II) and by $R^{01'}$ in the above general formula (II') and the substituent optionally present in the ring structure formed by connecting $R^{01}$ and $R^{04}$ in the above general formula (II) include a hydroxyl group, a halogen atom, a cyano group, a $C_{6-30}$ aryl group, a $C_{1-8}$ alkyl group, and a $C_{1-8}$ alkoxy group. Note that, if $R^{01}$, $R^{02}$, $R^{03}$, $R^{04}$, or $R^{01'}$ is a $C_{1-4}$ alkyl group and also has a substituent containing carbon atoms, then the total number of carbon atoms in $R^{01}$, $R^{02}$, $R^{03}$, $R^{04}$, or $R^{01'}$, including those of the substituent, should be within the defined range of 1 to 4.

In the above general formula (II'): examples of the 5-membered ring that may contain a hetero atom include a cyclopentene ring, a cyclopentadiene ring, an imidazole ring, a thiazole ring, a pyrazole ring, an oxazole ring, an isoxazole ring, a thiophen ring, a furan ring, and a pyrrole ring; and examples of the 6-membered ring that may contain a hetero atom include a benzene ring, a pyridine ring, a piperazine ring, a piperidine ring, a morpholine ring, a pyrazine ring, a pyrone ring, and a pyrrolidine ring.

Among the cyanine compounds usable in the present invention, cyanine compounds wherein $R^1$ in the general formula (I) is a group represented by the general formula (II') and cyanine compounds wherein $R^3$ is a group represented by the general formula (II') are preferred because of their excellent light resistance; and cyanine compounds wherein all of $R^1$ to $R^4$ are groups represented by the general formula (II') are even more preferable because they also have high solubility.

Moreover, cyanine compounds wherein the group represented by the general formula (II') is a group represented by general formula (IV) shown below are preferable because of their low production cost.

[Chem. 6]

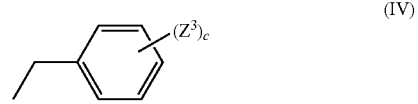

wherein, $Z^3$ represents a halogen atom, a hydroxyl group, a nitro group, a cyano group, a $C_{1-4}$ alkyl group that may optionally be substituted by a halogen atom, or a $C_{1-4}$ alkoxy group that may optionally be substituted by a halogen atom; and c represents a number of 0 to 5.

The cyanine compound used in the present invention has a resonance structure as shown below. The general formula (I) is representatively used to describe the cyanine compound according to the invention, but the cyanine compound according to the invention also encompasses compounds represented by general formula (I') shown below.

Further, the cyanine compound used in the invention may have optical isomers, such as enantiomers, diastereomers, or racemates, in which the asymmetric carbon atoms to which the groups represented by $R^1$ and $R^2$, as well as $R^3$ and $R^4$, are respectively bonded serve as chiral centers. Of these optical isomers, the cyanine compound used in the present invention may be any optical isomer in isolated form, or a mixture of several optical isomers.

[Chem. 7]

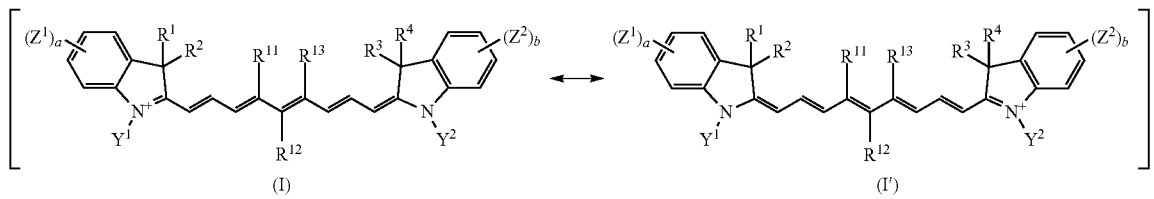

According to the cyanine compound used in the near-infrared-ray absorbing material of the invention, in the general formula (I), at least either $R^1$ is a group represented by the general formula (II) or (II'), or the anion represented by $An^{q-}$ is an ion represented by the general formula (III). Concrete examples of the cation moiety for when $R^1$ in the general formula (I) is represented by the general formula (II) or (II') include the following Compounds Nos. 1 to 60.

[Chem. 8]
Compound No. 1
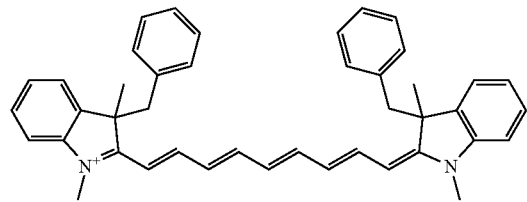
Compound No. 2
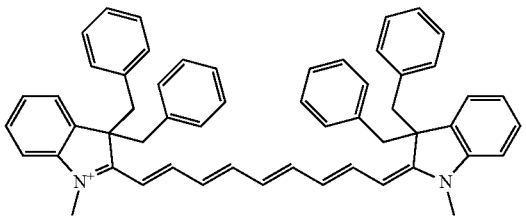
Compound No. 3
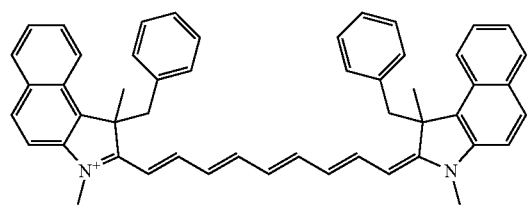
Compound No. 4
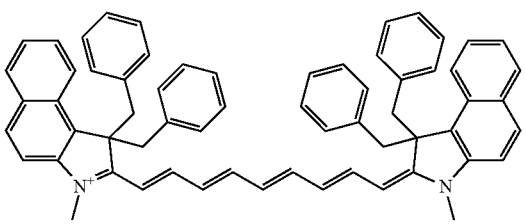
Compound No. 5
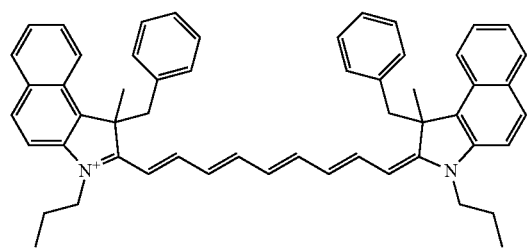
Compound No. 6
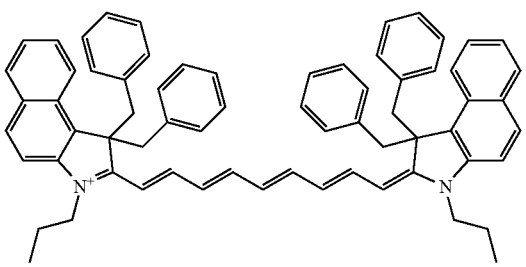
Compound No. 7
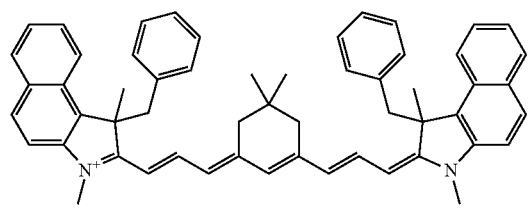
Compound No. 8
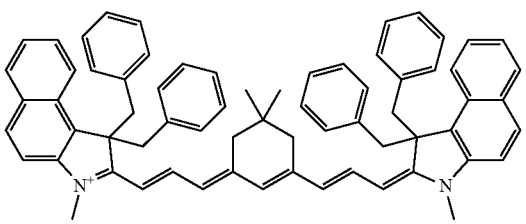
Compound No. 9
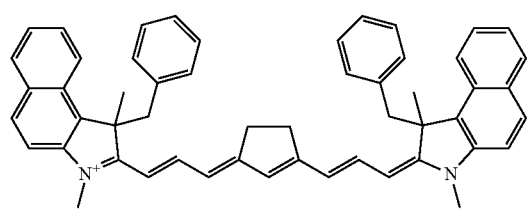
Compound No. 10
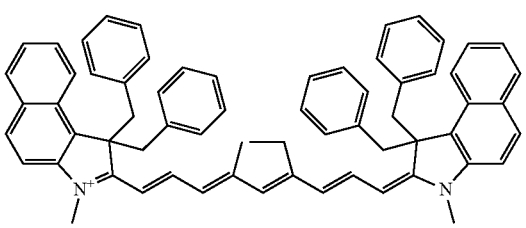
[Chem. 9]
Compound No. 11
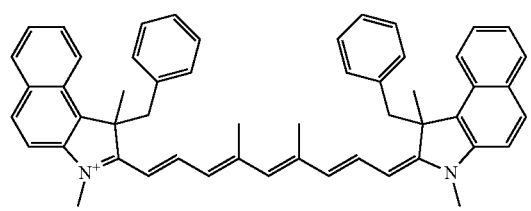
Compound No. 12
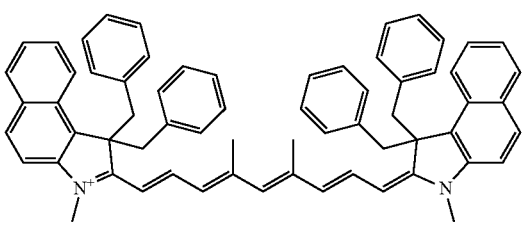

-continued
Compound No. 13
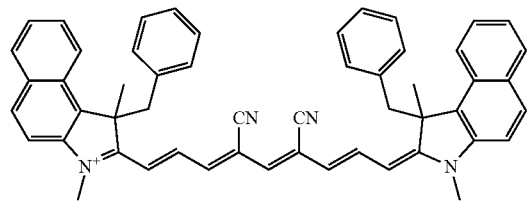
Compound No. 14
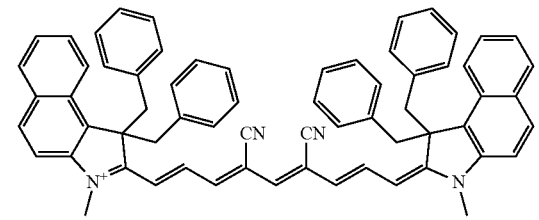
Compound No. 15
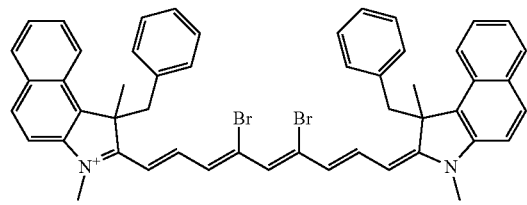
Compound No. 16
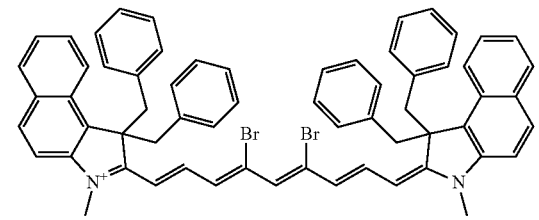
Compound No. 17
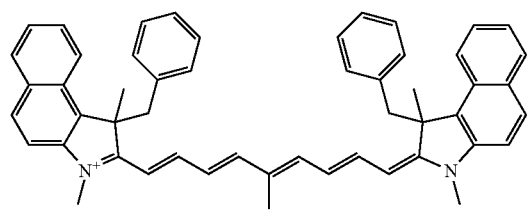
Compound No. 18
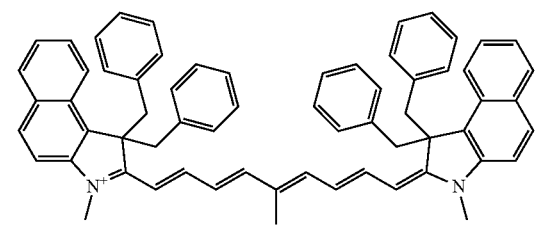
Compound No. 19
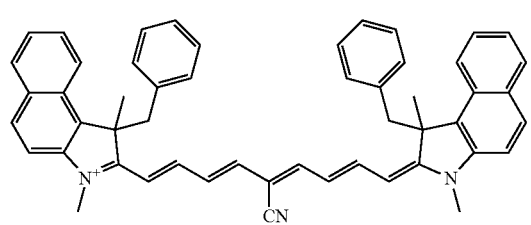
Compound No. 20
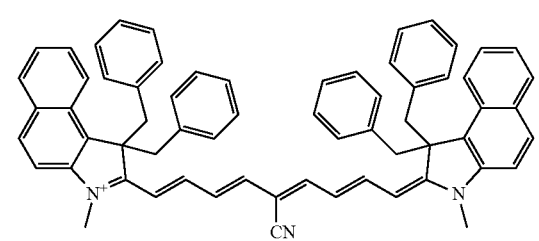
[Chem. 10]
Compound No. 21
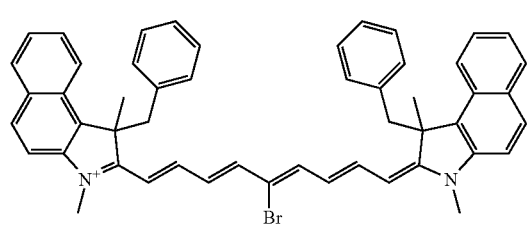
Compound No. 22
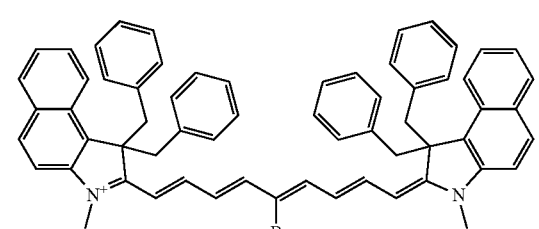
Compound No. 23
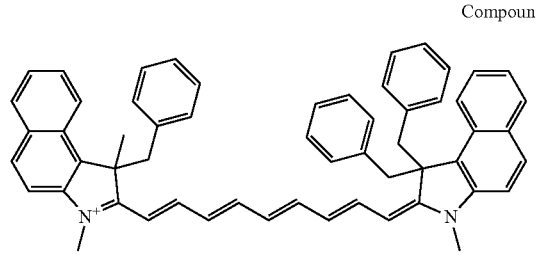
Compound No. 24
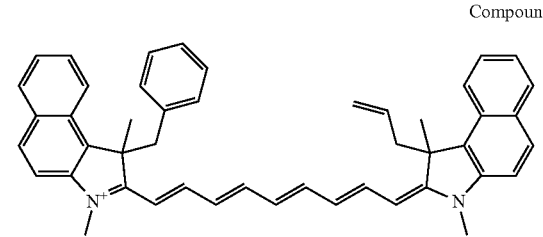

-continued
Compound No. 25
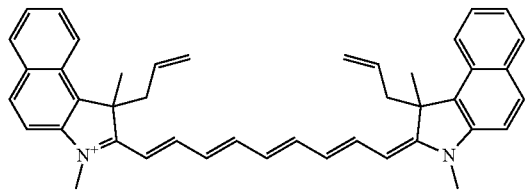
Compound No. 26
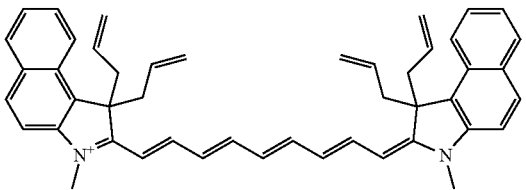
Compound No. 27
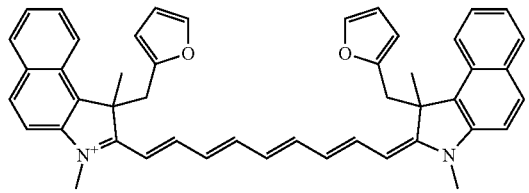
Compound No. 28
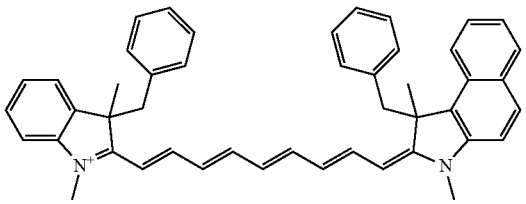
Compound No. 29
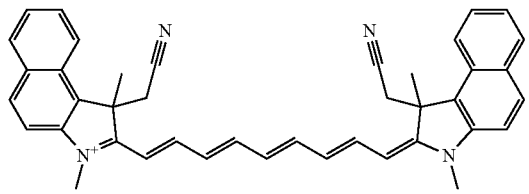
Compound No. 30
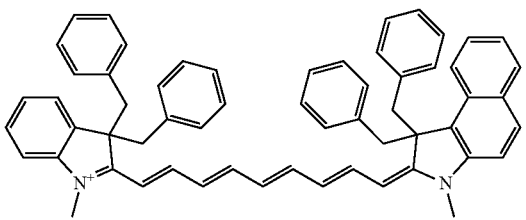
[Chem. 11]
Compound No. 31
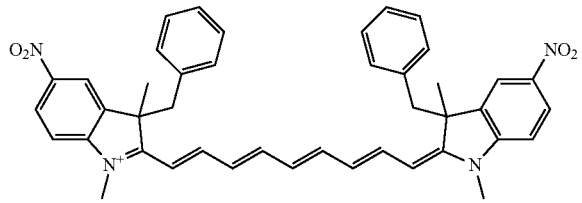
Compound No. 32
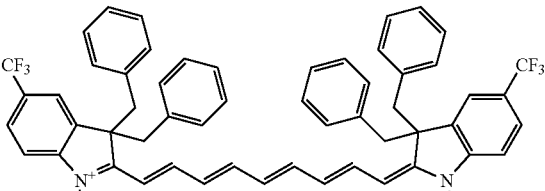
Compound No. 33
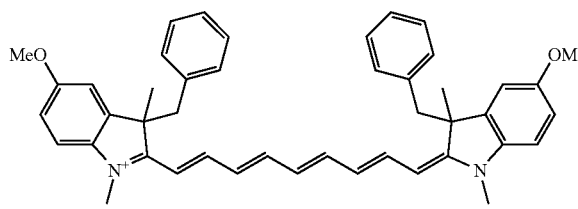
Compound No. 34
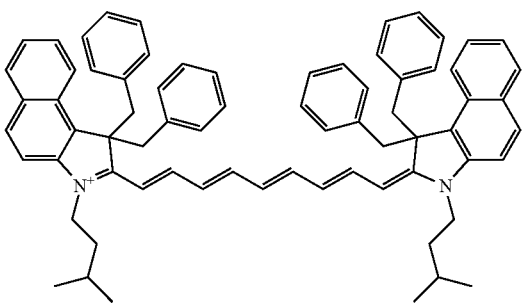
Compound No. 35
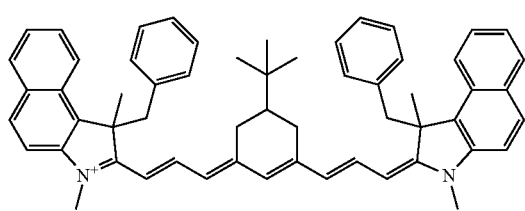
Compound No. 36
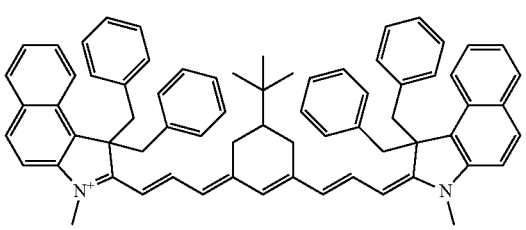

-continued
Compound No. 37
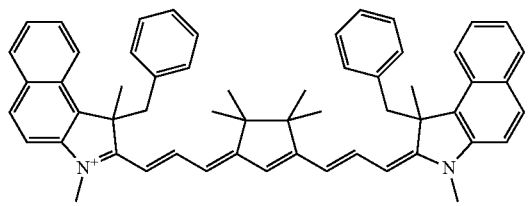
Compound No. 38
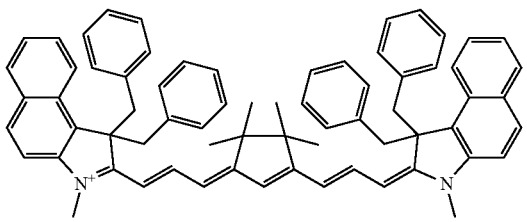
Compound No. 39
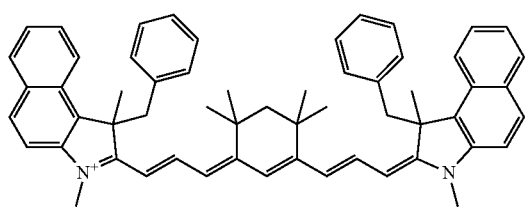
Compound No. 40
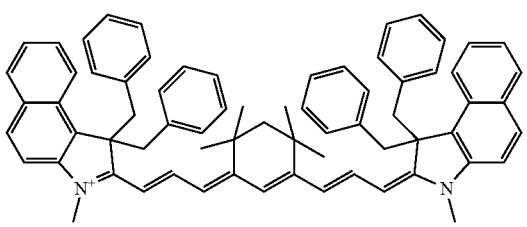
[Chem. 12A]
Compound No. 41
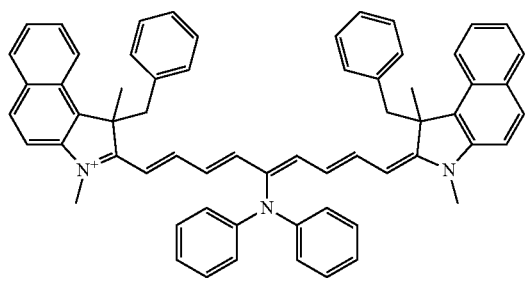
Compound No. 42
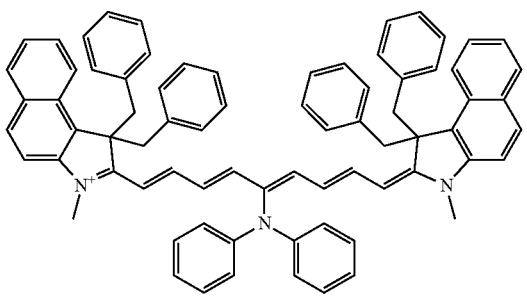
Compound No. 43
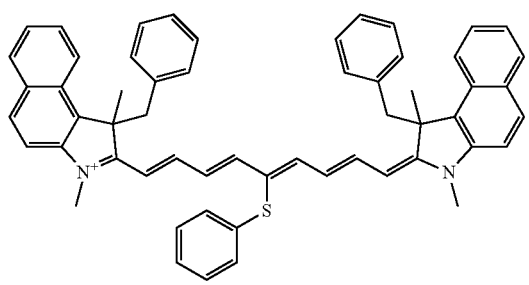
Compound No. 44
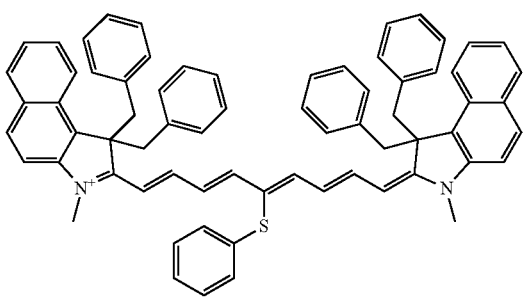
Compound No. 45
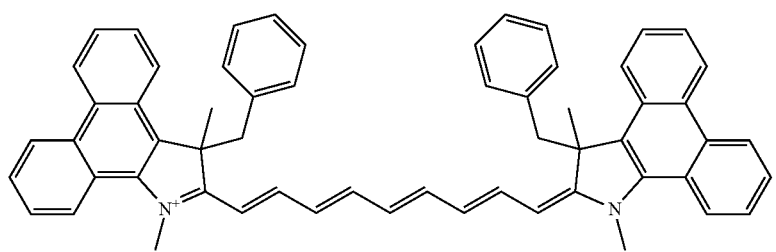

-continued
Compound No. 46
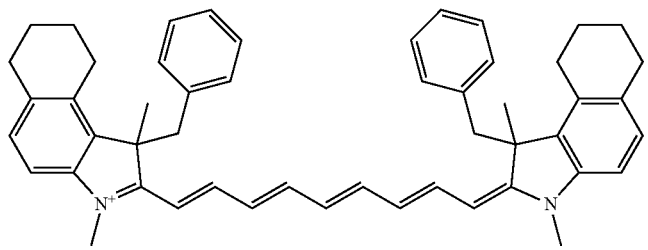
Compound No. 47
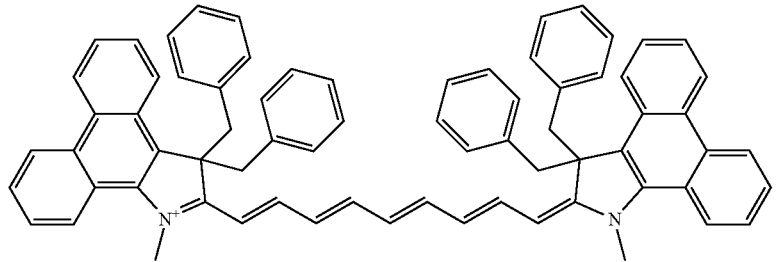
Compound No. 48
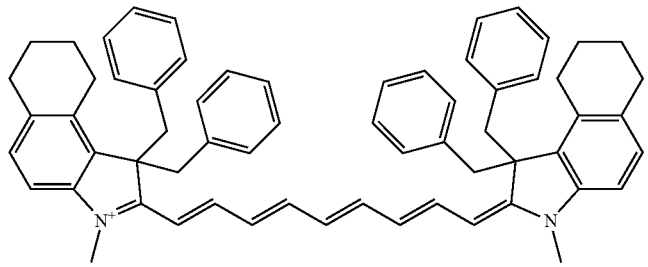
Compound No. 49
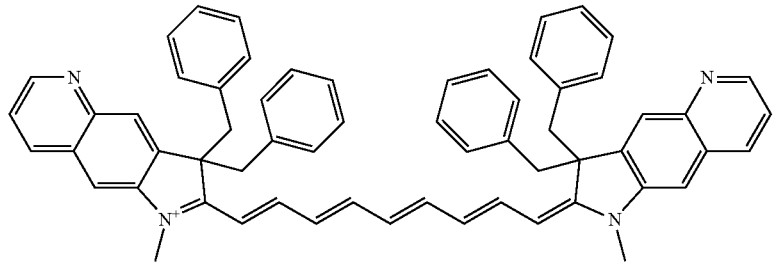
Compound No. 50
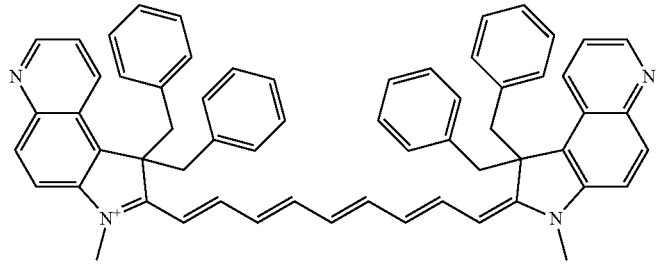
[Chem. 12B]
Compound No. 51
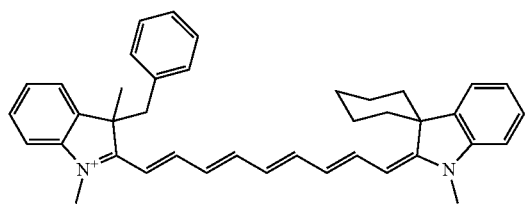
Compound No. 52
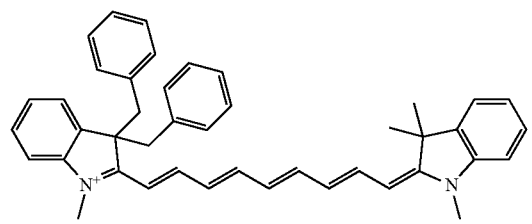

Compound No. 53

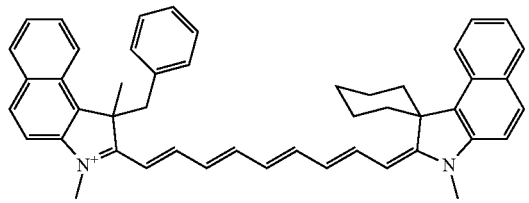

Compound No. 54

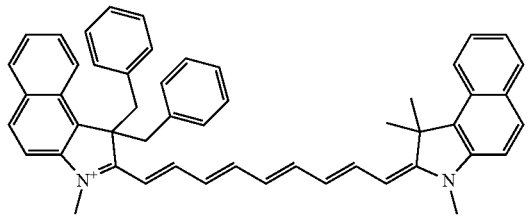

Compound No. 55

Compound No. 56

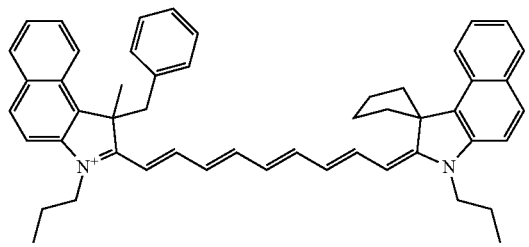

Compound No. 57

Compound No. 58

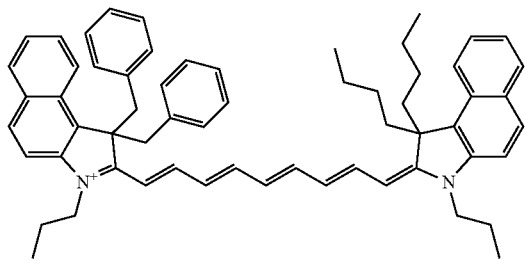

Compound No. 59

Compound No. 60

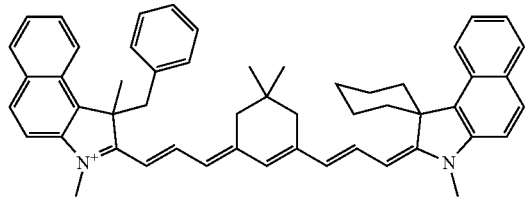

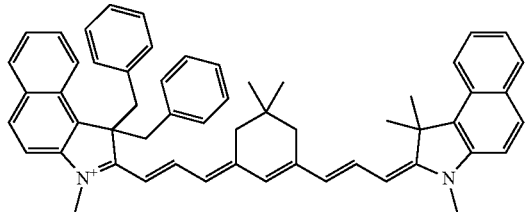

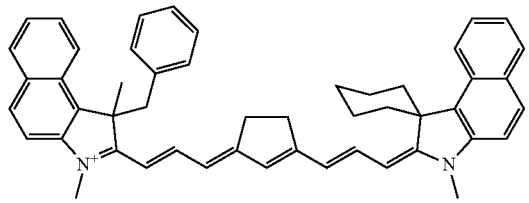

Concrete examples of cations, in the cyanine compound usable in the near-infrared-ray absorbing material of the invention, for when $R^1$ is not a group represented by the general formula (II) or (II') include the following Compounds Nos. 61 to 120, These cations can be employed in cases where the anion represented by An in the general formula (I) is an ion represented by the general formula (III).

[Chem. 12C]

Compound No. 61

Compound No. 62

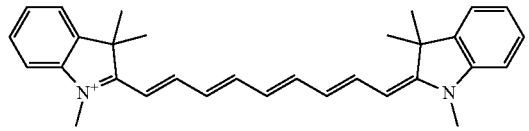

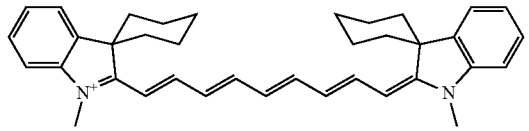

Compound No. 63

Compound No. 64

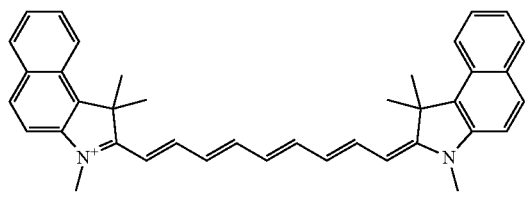

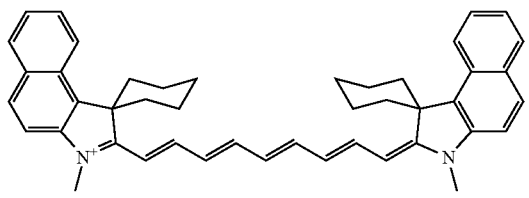

-continued
Compound No. 65
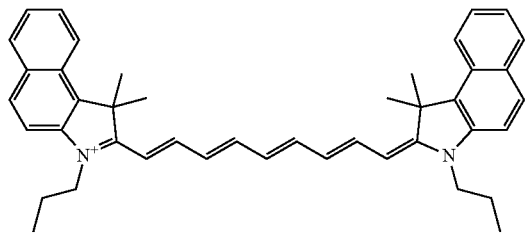
Compound No. 66
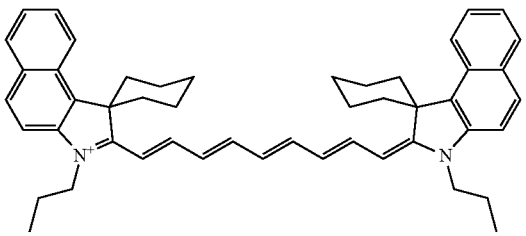
Compound No. 67
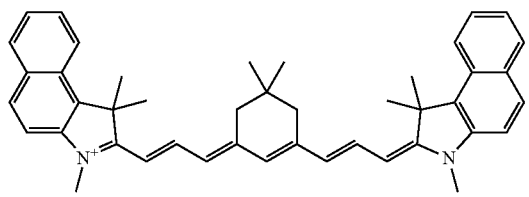
Compound No. 68
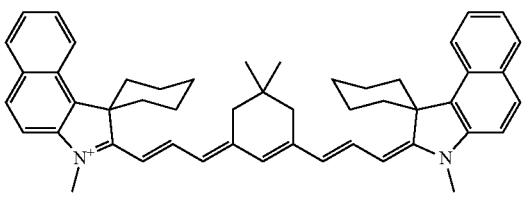
Compound No. 69
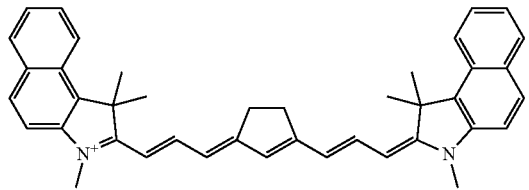
Compound No. 70
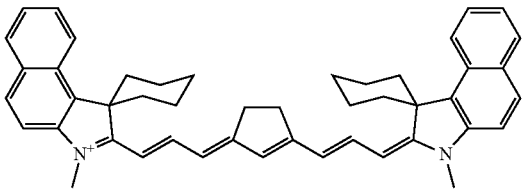
[Chem. 12D]
Compound No. 71
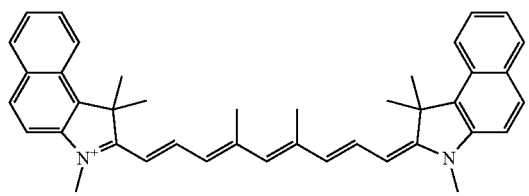
Compound No. 72
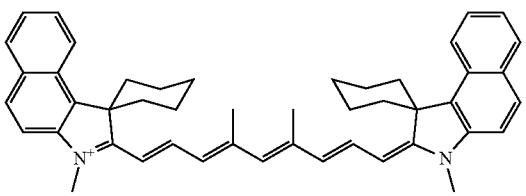
Compound No. 73
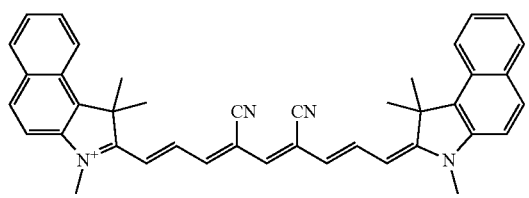
Compound No. 74
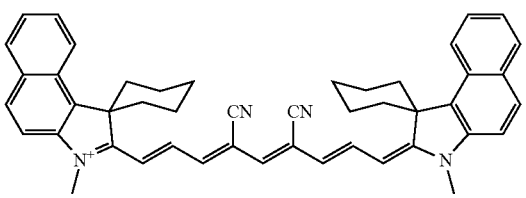
Compound No. 75
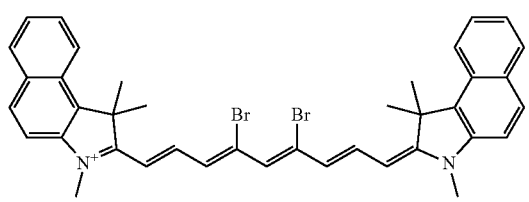
Compound No. 76
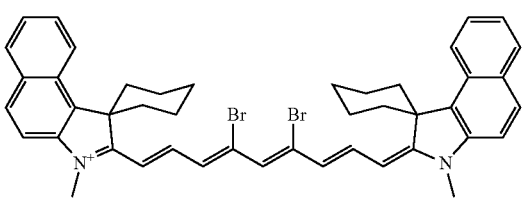
Compound No. 77
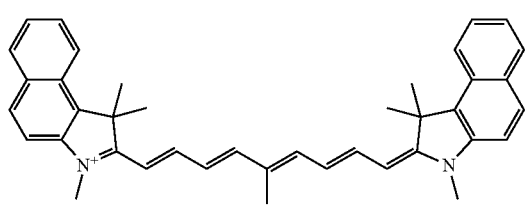
Compound No. 78
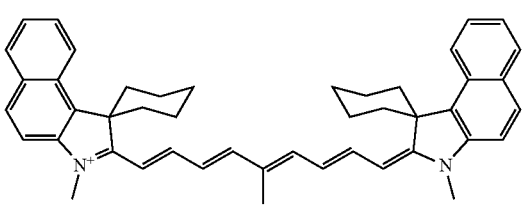

-continued
Compound No. 79
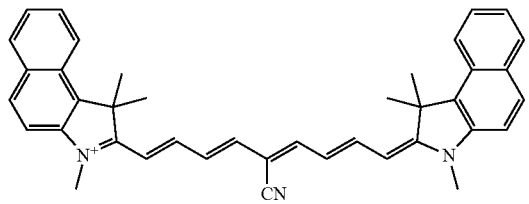
[Chem. 12E]
Compound No. 80
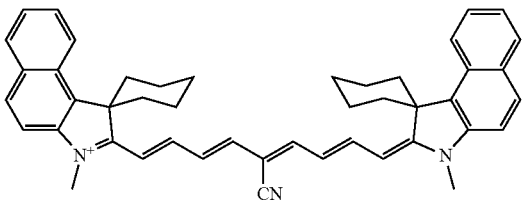
Compound No. 81
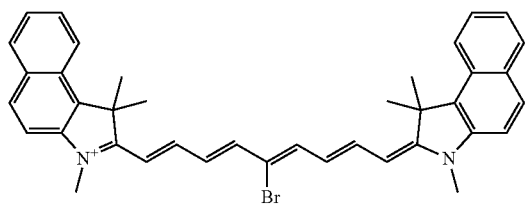
Compound No. 82
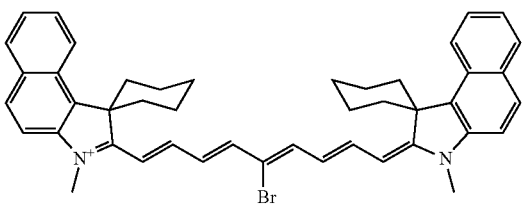
Compound No. 83
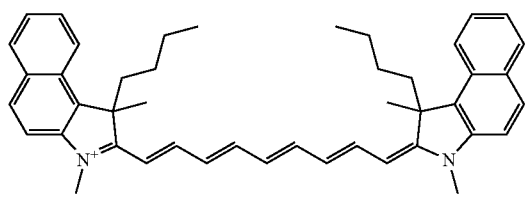
Compound No. 84
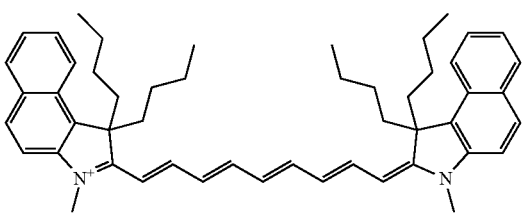
Compound No. 85
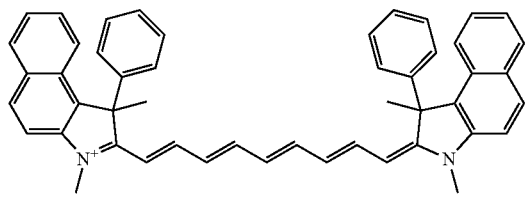
Compound No. 86
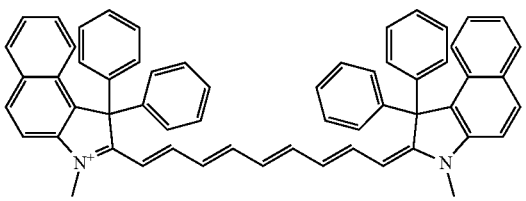
Compound No. 87
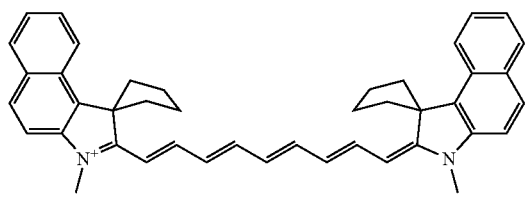
Compound No. 88
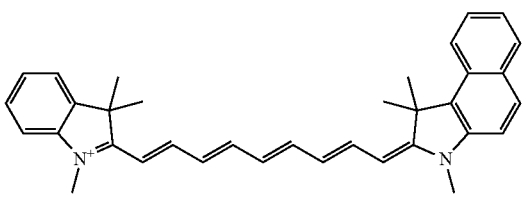
Compound No. 89
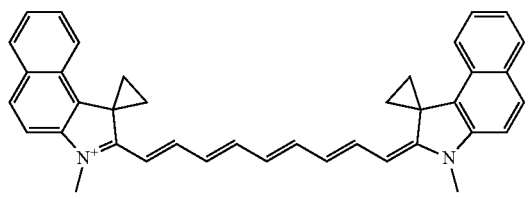
[Chem. 12F]
Compound No. 90
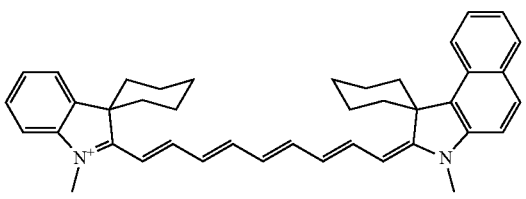
Compound No. 91
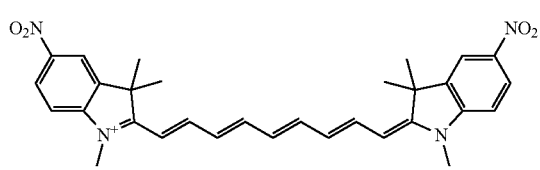
Compound No. 92
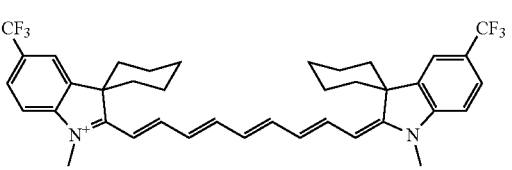

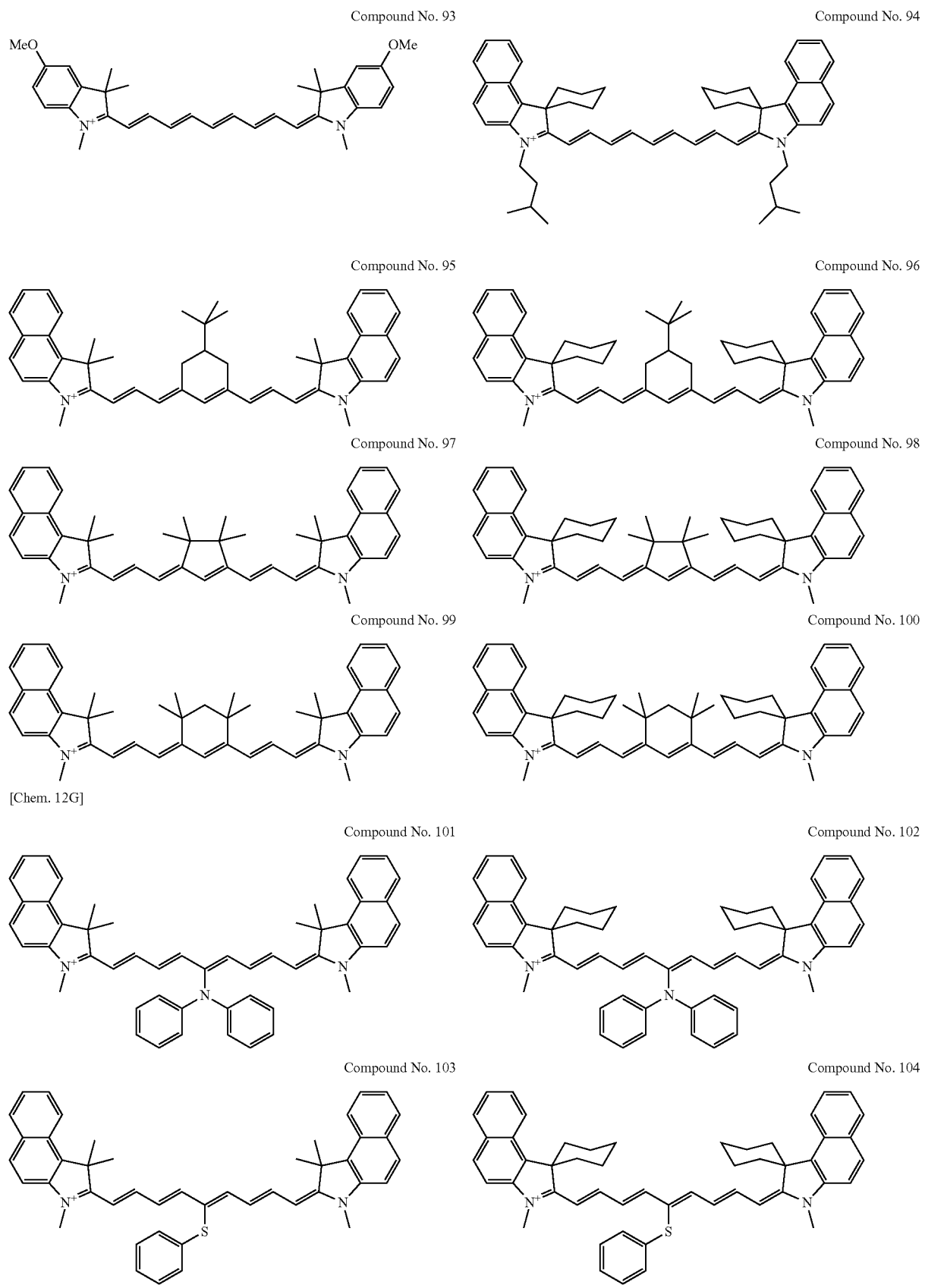

-continued
Compound No. 105
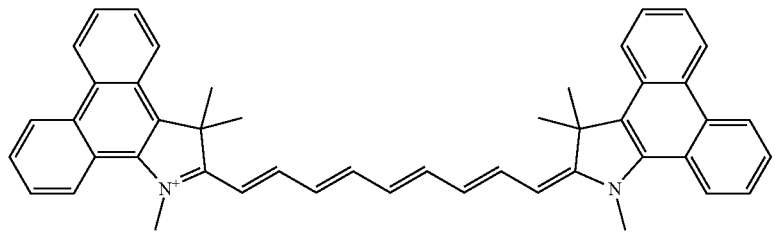
Compound No. 106
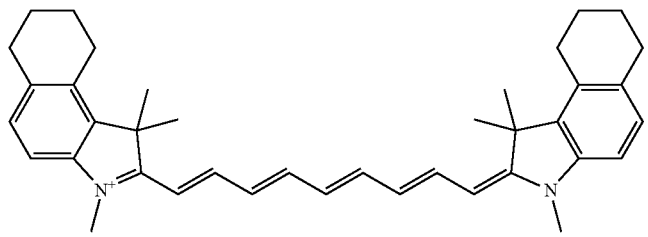
Compound No. 107
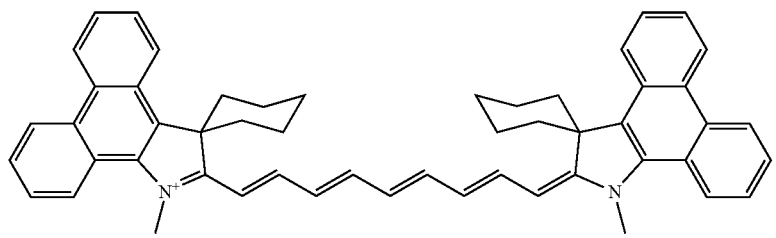
Compound No. 108
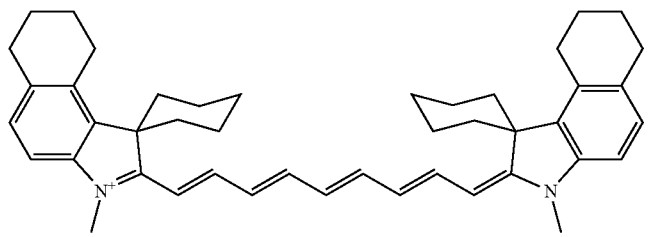
Compound No. 109
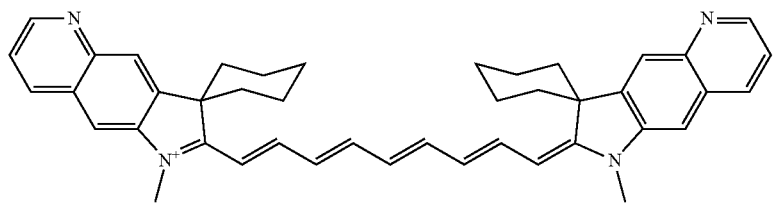
Compound No. 110
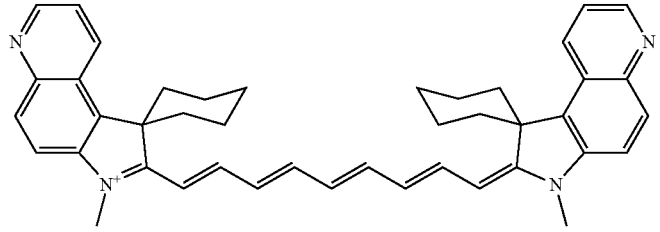
[Chem. 12H]
Compound No. 111
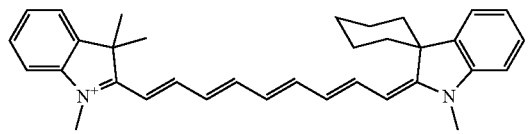
Compound No. 112
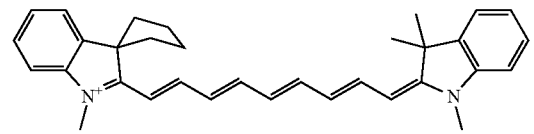

-continued

Compound No. 113

Compound No. 114

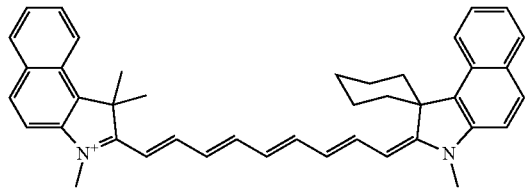
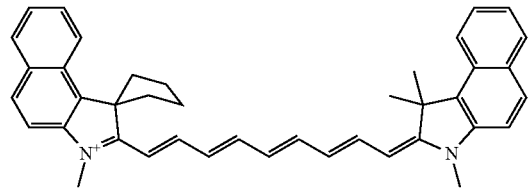

Compound No. 115

Compound No. 116

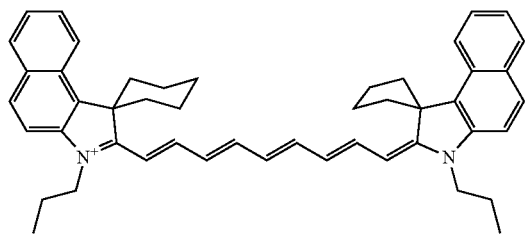
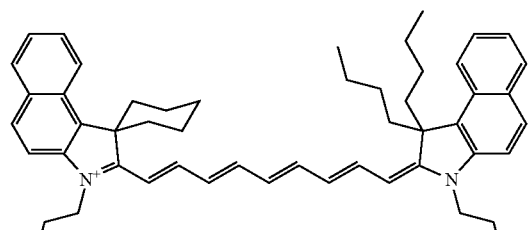

Compound No. 117

Compound No. 118

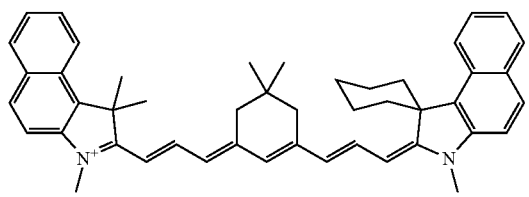
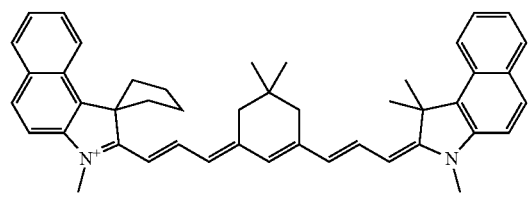

Compound No. 119

Compound No. 120

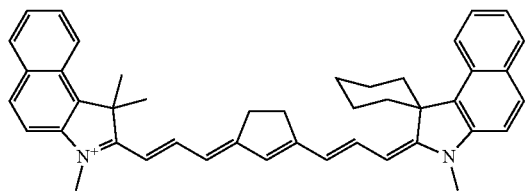

The cyanine compound represented by the general formula (I) usable in the present invention is not limited by how it is produced. For example, the cyanine compound can be produced by causing reaction between 2-methylindolenium salt derivatives and a bridging agent, such as an N,N'-diphenyl-heptane amidinium salt derivative, in the presence of triethylamine by the action of acetic anhydride.

In the formula, $R^1$, $R^2$, $R^3$, $R^4$, $R^{11}$, $R^{12}$, $R^{13}$, $Y^1$, $Y^2$, $Z^1$, $Z^2$, a, b, $An^{q-}$, q, and p are the same as those in the general formula (I).

The near-infrared-ray absorbing material of the invention contains at least one cyanine compound represented by the general formula (I). The cyanine compound has an absorption maximum in the wavelength range between 800 and 1000 nm

[Chem. 13]

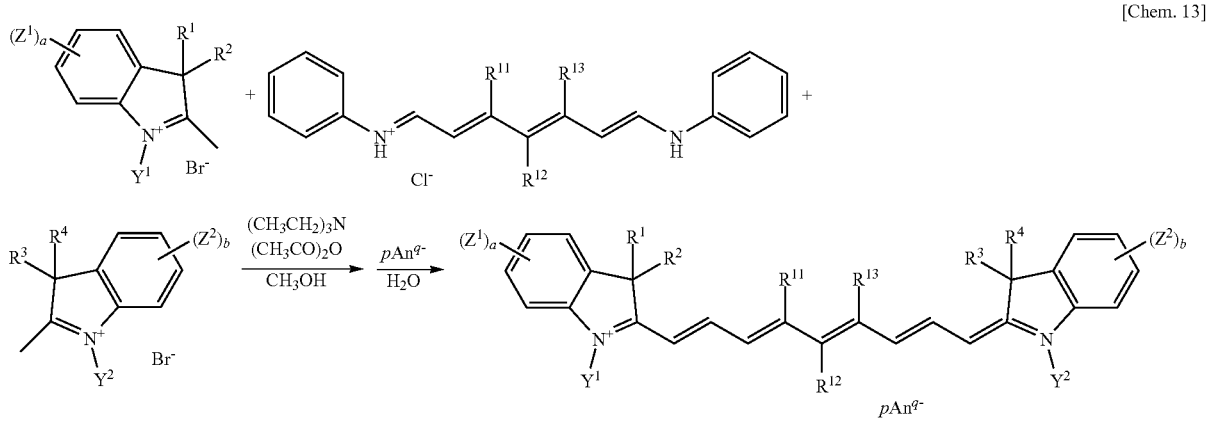

or in the vicinity thereof and can selectively absorb and block some of the visible light. The near-infrared-ray absorbing material of the invention containing this cyanine compound can therefore be suitably used especially for image-display-device optical filters for improving the quality of images displayed and for resin compositions for laser welding.

If necessary, the near-infrared-ray absorbing material of the invention may also combinedly contain a diimmonium compound. Any known diimmonium compound generally used as a near-infrared-ray absorbing compound in optical filters may be employed herein. In cases of combinedly using a diimmonium compound, it is preferable to use a diimmonium compound having the same anion as the cyanine compound because the near-infrared-ray absorbing material can be improved in stability. The content of the diimmonium compound in the present near-infrared-ray absorbing material is not particularly limited, but is preferably 1000 parts by weight or less with respect to 100 parts by weight of the cyanine compound from the standpoint of allowing the effects of the cyanine compound to be exerted sufficiently.

Compounds represented by general formula (IV) shown below can preferably be used as the diimmonium compound.

[Chem. 14]

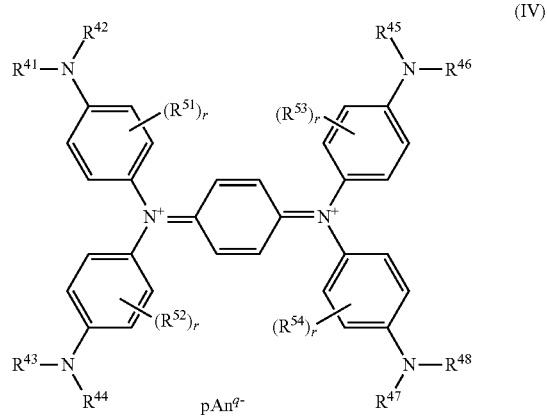

(IV)

In the formula, $R^{41}$, $R^{42}$, $R^{43}$, $R^{44}$, $R^{45}$, $R^{46}$, $R^{47}$, and $R^{48}$ each independently represent a hydrogen atom, a halogen atom, a $C_{1-8}$ alkyl group, or an independently represent a hydrogen atom, a halogen atom, a $C_{1-8}$ alkyl group, or an amino group; the $C_{1-8}$ alkyl group represented by $R^{41}$, $R^{42}$, $R^{43}$, $R^{44}$, $R^{45}$, $R^{46}$, $R^{47}$, $R^{48}$, $R^{51}$, $R^{52}$, $R^{53}$, and $R^{54}$ and the amino group represented by $R^{51}$, $R^{52}$, $R^{53}$, and $R^{54}$ may optionally have a substituent; a methylene group in the $C_{1-8}$ alkyl group may optionally be replaced by —O— or —CH=CH—; r represents a number of 1 to 4; and An, p, and q are the same as those in the general formula (I).

The near-infrared-ray absorbing material of the invention may be in the form of a solution by being mixed with an organic solvent. In this case, the solids content in the present near-infrared-ray absorbing material is preferably 0.01% to 50% by weight. Usable examples of the organic solvent include organic solvents usable in film-forming compositions that will be described further below. The present near-infrared-ray absorbing material may further contain necessary amounts of optional additives, such as tackifiers, softeners, light-resistance imparting agents, UV absorbers, antioxidants, plasticizers, antifoaming agents, leveling agents, dispersing agents, and curing agents. The content of these additives is not particularly limited and can be selected as appropriate depending on the usage etc. of the present near-infrared-ray absorbing material, but is preferably 10% by weight or less in the solids content.

A typical composition example of the near-infrared-ray absorbing material of the invention may be as follows:
Composition:
Cyanine compound represented by general formula (I): 0.5 to 100 parts by mass
Organic solvent: 0 to 100 parts by mass (preferably 0 to 50 parts by mass)
Diimmonium compound: 0 to 1000 parts by mass
Optional additive(s): 0 to 10 parts by mass The near-infrared-ray absorbing material of the invention may suitably be used for preparing optical filters for various applications, such as for image display devices, e.g. liquid crystal displays (LCDs), plasma display panels (PDPs), electroluminescence displays (ELDs), cathode-ray tube displays (CRTs), CCD image sensors, CMOS sensors, fluorescent display tubes, and field emission displays; for analytical equipment; for manufacturing semiconductor devices; for astronomical observations; for optical communication; for eyeglass lenses; and for windows. The optical filter is prepared using a film-forming composition made by blending the near-infrared-ray absorbing material of the invention with other components, such as an organic solvent, a transparent support material, an adhesive, and/or various polymers. The present near-infrared-ray absorbing material may also be suitably used for resin compositions for laser welding.

When employed in an image display device, the optical filter is usually arranged on the front face of the display. For example, the optical filter may be attached directly to the surface of the display, or in cases where a front panel is provided on the front-side of the display, the optical filter may be attached to the front surface (outer side) or the back surface (display side) of the front panel.

Next, a film-forming composition and an optical filter made using the film-forming composition of the present invention will be described in detail.

The film-forming composition of the invention can suitably be used as a material for making an optical filter. The present film-forming composition contains the near-infrared-ray absorbing material of the invention and also contains other components necessary for forming an optical filter (such as base materials, e.g. transparent support materials, adhesives, or various polymers, various additives, and organic solvents) which will be described in detail further below. Primary components to be contained are organic solvent(s) and base material(s) such as transparent support materials, adhesives, or various polymers.

The content of the present near-infrared-ray absorbing material in the present film-forming composition is such an amount that the content of the cyanine compound represented by the general formula (I) is preferably 0.0001% to 50% by mass, more preferably 0.001% to 5% by mass, in the solids content contained in the film-forming composition.

The content of the base material, such as transparent support materials, adhesives, or various polymers, is preferably 0.1% to 99% by mass, more preferably 1% to 80% by mass, in the solids content contained in the present film-forming composition.

In cases where an optical filter is produced by coating the present film-forming composition, the present film-forming composition is made into the form of a coating fluid by adding an organic solvent to the present film-forming composition. The concentration (in solids content) of the coating fluid is preferably 0.1% to 100% by mass, more preferably 1% to 25% by mass.

The above-mentioned organic solvent is not particularly limited, and various known solvents may be used as appropriate. Examples include: alcohols such as isopropanol; ether-alcohols such as methyl cellosolve, ethyl cellosolve, butyl cellosolve, and butyl diglycol; ketones such as acetone, methyl ethyl ketone, methylisobutyl ketone, cyclohexanone, and diacetone alcohol; esters such as ethyl acetate, butyl acetate, and methoxyethyl acetate; acrylates such as ethyl acrylate and butyl acrylate; fluorinated alcohols such as 2,2,3,3-tetrafluoropropanol; hydrocarbons such as hexane, benzene, toluene, and xylene; and chlorinated hydrocarbons such as methylene dichloride, dichloroethane, and chloroform. The organic solvent(s) may be used singly or mixed.

The optical filter of the present invention has a layer made of the film-forming composition including the near-infrared-ray absorbing material of the invention containing the cyanine compound.

The structure of the optical filter of the invention is not particularly limited, but usually has, on a transparent support, various layers such as an undercoat layer, an anti-reflection layer, a hard-coat layer, a lubricating layer, and a protective layer as necessary. The cyanine compound of the invention as well as other optional components such as various stabilizers and light absorbers, which are colorant compounds other than the present cyanine compound, may be included in the optical filter of the present invention by such methods as: (1) including the compounds/components in the transparent support or any given layer; (2) coating the compounds/components on the transparent support or any given layer; (3) including the compounds/components in an adhesive layer provided between any two adjacent layers selected from the transparent support and the various layers; or (4) providing a light-absorbing layer containing light absorbers, including the cyanine compound relating to the present invention, in addition to the various layers.

In cases of including the cyanine compound relating to the present invention in a given layer according to the above-described method (1), or coating the present cyanine compound according to the above-described method (2), or including the present cyanine compound in an adhesive layer according to the above-described method (3), or providing a light-absorbing layer according to the above-described method (4), an optical filter of the desired structure can be produced by, for example, making the film-forming composition into a coating fluid and coating it on the transparent support or any given layer. In cases of including the cyanine compound relating to the present invention in the transparent support according to the above-described method (1), a near-infrared-ray absorbing material containing the cyanine compound relating to the present invention may be blended to a transparent support material to form a film-forming composition, the film-forming composition may be made into pellets, and those pellets may be shaped into a film.

In the optical filter of the invention, and particularly in an optical filter for image-display purposes, the usage amount of the cyanine compound relating to the present invention represented by the general formula (I) per unit area of the optical filter is generally 1 to 1000 mg/m$^2$, and preferably 5 to 100 mg/m$^2$. A usage amount of less than 1 mg/m$^2$ cannot achieve sufficient light-absorbing effects, whereas a usage amount of over 1000 mg/m$^2$ may make the color of the filter too strong and impair display quality, etc., and may also lower the brightness. Note that, when using a mixture of several types of cyanine compounds as the cyanine compound relating to the present invention, the above "usage amount of the cyanine compound" relating to the invention refers to the total amount of all the cyanine compounds.

The content of the diimmonium compound combinedly used as necessary is 10 to 10000 mg/m$^2$, preferably 50 to 1000 mg/m$^2$, per unit area of the optical filter.

The optical filter of the invention may further contain other optional components, such as light absorbers other than the cyanine compound relating to the invention, IR absorbers, UV absorbers, phenol-based, phosphorus-based, sulfur-based or other antioxidants, flame retardants, slip additives, antistatic agents, inorganic particulates, light-resistance imparting agents, aromatic nitroso compounds, aminium compounds, iminium compounds, transition metal chelate compounds, and fillers.

In cases where the optical filter of the invention is to contain such other optional components as various stabilizers and light absorbers, which are colorant compounds other than the cyanine compound relating to the invention, such optional components may be added to the film-forming composition together with the cyanine compound relating to the invention and be included in the same layer as the cyanine compound relating to the invention according to one of the above-described methods (1) to (4), or such optional components may be included in a different layer from the cyanine compound relating to the invention by mutatis mutandis application of one of the above-described methods (1) to (4).

Examples of light absorbers other than the cyanine compound relating to the invention include light absorbers for color-tone adjustment and light absorbers for preventing reflection and/or glare of external light in cases where the optical filter is to be used for image display devices, and include light absorbers for preventing malfunction of infrared remote controllers in cases where the image display device is a plasma display.

Examples of the light absorbers for color-tone adjustment include light absorbers used for removing orange light in the 550-600 nm wavelength range, such as: trimethine cyanine derivatives such as trimethine indolium compounds, trimethine benzooxazolium compounds, and trimethine benzothiazolium compounds; pentamethine cyanine derivatives such as pentamethine oxazolium compounds and pentamethine thiazolium compounds; squarylium dye derivatives; azomethine dye derivatives; xanthene dye derivatives; azo dye derivatives; oxonol dye derivatives; benzylidene dye derivatives; pyrromethene dye derivatives; azo metal complex derivatives; rhodamine dye derivatives; phthalocyanine derivatives; porphyrin derivatives; and dipyrromethene metal chelate compounds.

Examples of the light absorbers (absorbing the 480-500 nm wavelength range) for preventing reflection and/or glare of external light include: trimethine cyanine derivatives such as trimethine indolium compounds, trimethine oxazolium compounds, trimethine thiazolium compounds, and indolidene trimethine thiazonium compounds; phthalocyanine derivatives; naphthalocyanine derivatives; porphyrin derivatives; and dipyrromethene metal chelate compounds.

Examples of the light absorbers (absorbing the 750-1100 nm wavelength range) for preventing malfunction of infrared remote controllers include: diimmonium compounds other than the compounds represented by the above general formula (IV); pentamethine cyanine derivatives such as pentamethine benzoindolium compounds, pentamethine benzooxazolium compounds, and pentamethine benzothiazolium compounds; heptamethine cyanine derivatives such as heptamethine indolium compounds, heptamethine benzoindolium compounds, heptamethine oxazolium compounds, heptamethine benzooxazolium compounds, heptamethine thiazolium compounds, and heptamethine benzothiazolium compounds; squarylium derivatives; nickel complexes such as bis(stilbenedithiolato) compounds, bis(benzenedithiolato) nickel compounds, and bis(camphordithiolato)nickel compounds; squarylium derivatives; azo dye derivatives; phthalocyanine derivatives; porphyrin derivatives; and dipyrromethene metal chelate compounds.

In the optical filter of the invention, the usage amount of each of the light absorber for color-tone adjustment, the light absorber for preventing reflection and/or glare of external light, and the light absorber (near-infrared-ray absorber) for preventing malfunction of infrared remote controllers usually ranges from 1 to 1000 mg/m$^2$, preferably from 5 to 100 mg/m$^2$, per unit area of the optical filter.

Examples of materials usable for the transparent support include inorganic materials such as glass; natural polymeric materials such as gelatin, casein, starch, cellulose derivatives, and alginic acid; and synthetic polymeric materials such as: cellulose esters such as diacetyl cellulose, triacetyl cellulose (TAC), propionyl cellulose, butyryl cellulose, acetylpropionyl cellulose, and nitrocellulose; polyamide; polyether; polyimide; polyurethane; polycarbonate; polyesters such as polyethylene terephthalate, polyethylene naphthalate, polybutylene terephthalate, poly-1,4-cyclohexanedimethylene terephthalate, polyethylene-1,2-diphenoxyethane-4,4'-dicarboxylate, and polybutylene terephthalate; polystyrene; polyolefins such as polyethylene, polypropylene, and polymethylpentene; acrylic resins such as polymethyl methacrylate; polysulfone; polyethersulfone; polyetherketone; polyetherimide; polyoxyethylene; norbornene resin; polyvinyl butyral; polyvinyl pyrrolidone; polyvinyl alcohol; polyvinyl chloride; styrene-butadiene copolymer; melamine resin; and cyclic olefin resins. The transmittance of the transparent support is preferably 80% or above, and more preferably 86% or above. The haze is preferably 2% or less, and more preferably 1% or less. The refractive index is preferably 1.45 to 1.70.

The transparent support may also contain inorganic particulates. Examples of the inorganic particulates include silicon dioxide, titanium dioxide, barium sulfate, calcium carbonate, talc, and kaoline.

The transparent support may be subjected to various surface treatments. Examples of the above-mentioned surface treatments include chemical treatment, mechanical treatment, corona discharge treatment, flame treatment, UV irradiation, high-frequency/microwave treatment, glow discharge treatment, active plasma treatment, laser treatment, treatment with mixed acid, and ozone oxidation.

In cases where a filter layer containing light absorber(s) is to be provided separately from the various layers, the undercoat layer that may be provided in the optical filter of the invention is used between the transparent support and the optical filter layer. The undercoat layer is formed either as a layer containing a polymer having a glass transition temperature of −60° C. to 60° C., as a layer whose surface on the filter-layer side is made coarse, or as a layer containing a polymer having an affinity for the polymer in the filter layer. Instead, the undercoat layer may be provided on the surface of a transparent support that does not have a filter layer with the aim of enhancing the bonding force between the transparent support and the layer provided thereon (e.g., the anti-reflection layer or the hard-coat layer), or enhancing the affinity between the optical filter and a bonding agent for bonding the optical filter to an image display device. The thickness of the undercoat layer is preferably 2 nm to 20 μm, more preferably 5 nm to 5 μm, even more preferably 20 nm to 2 μm, further more preferably 50 nm to 1 μm, and most preferably 80 nm to 300 nm. The undercoat layer, if it contains a polymer having a glass transition temperature of −60° C. to 60° C., bonds the transparent support and the filter layer together by means of the polymer's adhesiveness. For example, the polymer having a glass transition temperature of −60° C. to 60° C. can be prepared through polymerization or copolymerization of, for example, vinyl chloride, vinylidene chloride, vinyl acetate, butadiene, neoprene, styrene, chloroprene, acrylate, methacrylate, acrylonitrile, or methyl vinyl ether. The glass transition temperature is preferably 50° C. or below, more preferably 40° C. or below, even more preferably 30° C. or below, further more preferably 25° C. or below, and most preferably 20° C. or below. The modulus of elasticity of the undercoat layer at 25° C. is preferably 1 to 1000 MPa, even more preferably 5 to 800 MPa, and most preferably 10 to 500 MPa. The undercoat layer, if its surface on the filter-layer side is made coarse, serves to bond the transparent support and the filter layer together because the filter layer is formed on the coarse surface. The undercoat layer whose surface on the filter-layer side is made coarse can easily be made by coating of a polymer latex. The average particle size of the latex is preferably 0.02 to 3 μm, and more preferably 0.05 to 1 μm. Examples of the polymer having an affinity for the binder polymer in the filter layer include acrylic resin, cellulose derivatives, alginic acid, gelatin, casein, starch, polyvinyl alcohol, polyvinyl butyral, polyvinyl pyrrolidone, soluble nylon, and polymer latices. The optical filter of the present invention may also have two or more undercoat layers. The undercoat layer may include other additives, such as solvents for swelling the transparent support, matte agents, surfactants, antistatic agents, coating aids, and hardeners.

The anti-reflection layer that may be provided in the optical filter of the invention must have a low refractive-index layer. The refractive index of the low refractive-index layer is lower than the refractive index of the transparent support. The refractive index of the low refractive-index layer is preferably 1.20 to 1.55, and more preferably 1.30 to 1.50, The thickness of the low refractive-index layer is preferably 50 to 400 nm, and more preferably 50 to 200 nm. The low refractive-index layer can be formed as a layer comprising a low-refractive-index fluorine-containing polymer (disclosed in JP-A-57-34526, JP-A-3-130103, JP-A-6-115023, JP-A-8-313702, and JP-A-7-168004), as a layer prepared by sol-gel methods (disclosed in JP-A-5-208811, JP-A-6-299091, and JP-A-7-168003), or as a layer containing particulates (disclosed in JP-B-60-59250, JP-A-5-13021, JP-A-6-56478, JP-A-7-92306, and JP-A-9-288201). In cases of employing the above-mentioned layer containing particulates, voids can be formed in the low refractive-index layer as microvoids between or in the particulates. The layer containing particulates has a voidage of preferably 3 to 50 vol %, and more preferably 5 to 35 vol %.

In order to prevent reflection of light in a wide range of wavelengths, it is preferable to laminate layers having higher refractive index (medium and high refractive-index layers) in the anti-reflection layer in addition to the low refractive-index layer. The refractive index of the high refractive-index layer is preferably 1.65 to 2.40, and more preferably 1.70 to 2.20, The refractive index of the medium refractive-index layer is adjusted to a value intermediate between the refractive index of the low refractive-index layer and that of the high refractive-index layer. The refractive index of the medium refractive-index layer is preferably 1.50 to 1.90, and more preferably 1.55 to 1.70, The thickness of each of the medium and high refractive-index layers is preferably 5 nm to 100 μm, even more preferably 10 nm to 10 μm, and most preferably 30 nm to 1 μm. The haze of each of the medium and high refractive-index layers is preferably 5% or less, even more preferably 3% or less, and most preferably 1% or less. The medium and high refractive-index layers can be formed using a polymer binder having a relatively high refractive index. Examples of polymers having a high refractive index include polystyrene, styrene copolymers, styrene-butadiene copolymer, polyvinyl chloride, polycarbonate, polyamide, melamine resin, phenolic resin, epoxy resin, and polyurethane obtained by reacting cyclic (alicyclic or aromatic) isocyanate and a polyol. Other polymers having a cyclic (aromatic, heterocyclic, or alicyclic) group and polymers having a halogen atom, other than fluorine, as a substituent also have a high refractive index. It is also possible to use a polymer made by polymerization of a monomer that is introduced with a double bond so that it can undergo radical curing.

Inorganic particulates may be dispersed in the polymer binder to obtain even higher refractive indices. The refractive index of the inorganic particulates is preferably 1.80 to 2.80. The inorganic particulates are preferably made of metal oxides or metal sulfides. Examples of metal oxides/sulfides include titanium oxide (e.g., rutile, a mixed crystal of rutile and anatase, anatase, or an amorphous structure), tin oxide, indium oxide, zinc oxide, zirconium oxide, and zinc sulfide. Among these, titanium oxide, tin oxide, and indium oxide are particularly preferred. The inorganic particulates may employ the above-mentioned metal oxide or metal sulfide as a main component and also contain other elements. Herein, "main component" refers to a component having the largest content (% by mass) among the components constituting the particulates. Examples of other elements include Ti, Zr, Sn, Sb, Cu, Fe, Mn, Pb, Cd, As, Cr, Hg, Zn, Al, Mg, Si, P, and S. Further, the medium and high refractive-index layers may be made using a film-formable inorganic material that is either dispersible in a solvent or is itself in liquid form, such as an alkoxide of various elements, a salt of an organic acid, a coordination compound (e.g., a chelate compound) bonded to a coordinating compound, or an active inorganic polymer.

The surface of the anti-reflection layer may be provided with an anti-glare function (function of preventing the surrounding scenes around the film from being reflected in the film surface by scattering the incident light at the surface). The anti-reflection layer can be provided with the anti-glare function by, for example: forming fine projections and depressions on the surface of a transparent film to form the anti-reflection layer on that surface; or first forming an anti-reflection layer and then forming projections and depressions on the surface thereof using an emboss roll. The anti-reflection layer having an anti-glare function generally has a haze of 3% to 30%.

The hard-coat layer that may be provided in the optical filter of the invention has hardness higher than that of the transparent support. The hard-coat layer preferably contains a cross-linked polymer. The hard-coat layer may be made using, for example, acrylic, urethane-based, or epoxy-based polymers, oligomers, or monomers (e.g. UV curable resins). Silica-based materials may also be used for forming the hard-coat layer.

The surface of the anti-reflection layer (low refractive-index layer) may have a lubricating layer. The lubricating layer serves to provide slipperiness to the surface of the low refractive-index layer and improve scratch resistance. The lubricating layer may be made using, for example, polyorganosiloxane (e.g. silicone oil), natural wax, petroleum wax, metal salts of higher fatty acids, fluorine-based lubricants, or derivatives thereof. The thickness of the lubricating layer is preferably 2 to 20 nm.

In cases where the above-described method "(3) including the compounds/components in an adhesive layer provided between any two adjacent layers selected from the transparent support and the various layers" is employed in including the cyanine compound relating to the invention in the optical filter, the present cyanine compound and other components can simply be added to an adhesive, and that adhesive can be used to bond together any two adjacent layers selected from the transparent support and the various layers.

Examples of usable adhesives include known, clear bonding agents for laminated glass, such as silicone adhesives, urethane adhesives, acrylic adhesives, polyvinyl butyral bonding agents, polyvinyl ether adhesives, ethylene-vinyl acetate adhesives, polyolefin adhesives, SBR adhesives, and rubber-based adhesives. Among them, acrylic adhesives, and particularly acidic acrylic adhesives, are preferably used. The thickness of the adhesive layer is preferably 2 to 400 µm.

The acrylic adhesives are not particularly limited, and usable examples include: homopolymers of monomers having a reactive functional group, such as a carboxyl, hydroxyl, amide, amino, or epoxy group, and an ethylenic unsaturated double bond; copolymers made by combining several types of the above monomers; or copolymers of the above monomers having a reactive functional group and an ethylenic unsaturated double bond and monomers having an ethylenic unsaturated double bond, such as (meth)acrylic monomers and vinyl monomers. It is also possible to use adhesives that contain, as curing agents to enhance cohesion of the adhesives as necessary, cross-linking agents such as metal chelate compounds, isocyanate-type compounds, melamine compounds, epoxy-type compounds, amine-type compounds, aziridine-type compounds, and oxazoline compounds.

Commercially-available acrylic adhesives may be used, and examples include "DB-Bond 5541" (product of Diabond Industry Co., Ltd.), "SK-Dyne AS-1925, KP-2230, and SK-1811L" (product of Soken Chemical & Engineering Co., Ltd.), "DX2-PDP-19" (product of Nippon Shokubai Co., Ltd.), "AT-3001" (product of Saiden Chemical Industry Co., Ltd.), "Oribain BPS5896" (product of Toyo Ink Mfg. Co., Ltd.), and "CS-9611" (product of Nitto Denko Corporation).

In cases of employing the above-described method "(4) providing a light-absorbing layer containing light absorbers, including the cyanine compound relating to the present invention, in addition to the various layers," the cyanine compound relating to the invention may be used as-is to form the light-absorbing layer, or instead, the light-absorbing layer may be formed by first dispersing the light absorbers including the present cyanine compound in a binder. Examples of the binder include those given as examples for the transparent support material. The binder may be used together with an organic solvent, examples of which include those given as examples of organic solvents includable in the above-described film-forming composition.

The above-described undercoat layer, anti-reflection layer, hard-coat layer, lubricating layer, filter layer, and others, may be formed through general application methods. Examples of application methods include dip coating, air knife coating, curtain coating, roller coating, wire-bar coating, gravure coating, and extrusion coating using a hopper (disclosed in specification of U.S. Pat. No. 2,681,294A). Two or more layers may be formed through simultaneous application. Simultaneous application methods are disclosed in U.S. Pat. Nos. 2,761,791A, 2,941,898A, 3,508,947A, and 3,526,528A. Mention is also made in Yuji Harazaki, "Coating Engineering" (Asakura Publishing Co., Ltd., 1973), p. 253.

Next, the resin composition for laser welding of the present invention will be described in detail.

Laser welding is for welding and joining resin parts together by laser irradiation. Generally, one of the parts to be joined is a light-transmitting resin part (transmitting part), and the other is a light-absorbing resin part (absorbing part)

that absorbs the laser beams and generates heat. The two parts are placed on one another and irradiated with laser beams from the transmitting-part side, which causes the absorbing part to melt. The heat is then transmitted from the periphery of the molten absorbing part to the transmitting part, which causes the transmitting part to melt as well, resulting in joining of the two parts.

The resin composition for laser welding of the invention is a composition including the near-infrared-ray absorbing material of the invention containing the cyanine compound and is thus used for forming the above-described absorbing part. Formation of the transmitting part, on the other hand, is done by using a resin composition prepared by blending, to a binder resin (light-transmitting resin), such components as organic solvents, color-developing components, and colorant components as necessary in such amounts that will not inhibit the laser-beam transmissibility. The resin composition for laser welding of the invention can be prepared by adding the infrared-ray absorbing material of the invention to the above-described resin composition usable for forming the transmitting part. The resin composition for laser welding of the invention may further contain other near-infrared-ray absorbing substances as necessary. The present laser-weldable resin composition, which contains the cyanine compound relating to the present invention, is highly sensitive to lasers and can thus achieve the desired joining with high accuracy and strength.

The binder resin is not particularly limited, and examples include: homopolymers or copolymers of acrylic acid-based monomers such as acrylic acid, acrylates, methacrylates, and methacrylates; cellulose-based polymers such as methyl cellulose, ethyl cellulose, and cellulose acetate; vinyl-based polymers, such as polystyrene, vinyl chloride-vinyl acetate copolymer, polyvinyl pyrrolidone, polyvinyl butyral, and polyvinyl alcohol, and copolymers of vinyl compounds; condensation polymers such as polyester and polyamide; rubber-type thermoplastic polymers such as butadiene-styrene copolymer; and polymers produced by polymerization/cross-linking of photopolymerizable compounds such as epoxy compounds. Examples of the organic solvent include those given as examples of organic solvents for the above-described film-forming composition.

Examples of the near-infrared-ray absorbing substances that may be used in the present laser-weldable resin composition in combination with the present near-infrared-ray absorbing material containing the cyanine compound represented by the general formula (I) include phthalocyanine-based compounds and other pigment- and dye-based colorants, such as: pigments like carbon black and aniline black; polymethine dyes (cyanine dyes) disclosed in "Near-Infrared-Ray Absorbing Dyes," *Kagaku Kogyo* (Chemical Industry), May 1986, pp. 45-51, and "Development and Market Trends of Functional Dyes of 1990s," CMC Publishing, 1990, Chapter 2, Section 2.3; phthalocyanine dyes; dithiol metal complex salt-based dyes; naphthoquinone- or anthraquinone-based dyes; triphenylmethane (analog)-based dyes; aminium- or diimmonium-based dyes; azo dyes; indoaniline metal complex dyes; and intermolecular CT dyes.

The resin composition for laser welding of the invention may further contain, as necessary, various other additives such as stabilizers, antioxidants, antistatic agents, waxes, anti-UV agents, flame retardants, and various fillers.

As for the color tone of the resin parts, it is preferable that the absorbing part is primarily colored black, whereas the transmitting part preferably has a dark color ranging from blue, purple, to black. The dark coloring can be achieved using a single dark-color colorant or a blend of colorants containing various colors. For example, red, yellow, and blue colorants may be blended to color the resin parts black.

The resin composition for laser welding of the invention may be made into pellets having the same color concentration as the target absorbing part, into color concentrates (color masterbatches) colored to have higher concentrations, or into single-color pellets. Pellets having the same color concentration as the target absorbing part can be used as-is to form/mold the absorbing part. Color concentrates can be mixed with natural resins in predetermined amounts at the time of forming/molding the absorbing part. Single-color pellets can be mixed with other resin pellets at the time of forming/molding the parts. Note that it goes without saying that the laser-weldable resin composition of the invention encompasses molded products formed/molded into desired shapes.

The resin composition for laser welding of the invention can be produced according to known methods for producing colored resins. For example, non-colored, binder-resin pellets may be mixed with predetermined amounts of colorants (the near-infrared-ray absorbing material of the invention, as well as other combinedly-usable near-infrared-ray absorbing substances, color-developing components, and colorant components), and the mixture may be molten and kneaded and produced into colored pellets with an extruder. Further, color concentrates can be made according to the same method by adding colorants in higher concentrations.

The colorant content in the resin composition for laser welding of the invention can be selected as appropriate depending on the degree of coloring of the target absorbing part and is not particularly limited. For example, a colorant content of 0.01 to 10 parts by mass per 100 parts by mass of binder resin is preferable when the resin composition is formed into an absorbing part or color concentrate; particularly for the cyanine compound relating to the invention, it is preferable to use the near-infrared-ray absorbing material of the invention in amounts such that the cyanine compound content is 0.01 to 1 part by mass per 100 parts by mass of binder resin. A colorant content of less than 0.01 parts by mass may not achieve a sufficient coloring concentration. As for the cyanine compound relating to the invention, a content of less than 0.01 parts by mass may result in insufficient improvement in laser-beam absorptivity. On the other hand, a colorant content exceeding 10 parts by mass will only saturate the coloring concentration, and as for the cyanine compound relating to the invention, a content exceeding 1 part by mass will not achieve further improvements in the laser-beam absorptivity; excessive amounts, in both cases, will lead to increase in costs, thus not preferable.

Examples of laser beams usable in performing laser welding using the laser-weldable resin composition of the present invention include glass:$Nd^{3+}$ lasers, YAG:$Nd^{3+}$ lasers, ruby lasers, helium-neon lasers, krypton lasers, argon lasers, $H_2$ lasers, $N_2$ lasers, and semiconductor lasers. Preferred among the above are YAG:$Nd^{3+}$ lasers.

The wavelength of the laser beam will differ depending on the parts to be welded and thus cannot be generally determined, but is preferably 1,060 nm or less. Wavelengths exceeding 1,060 nm may pose difficulty in fusing the joining surfaces of the two parts.

The laser beam output is preferably from 5 to 30 W. A laser beam output below 5 W is too low and may pose difficulty in fusing the joining surfaces of the two parts, whereas an output exceeding 30 W is too high and may lead to evaporation and/or degeneration of the parts.

Next, the cyanine compound of the invention will be described. The present cyanine compound is a compound in which $R^1$ in the general formula (I) is a group represented by the general formula (II) or (II'). The present cyanine compound is suitable as optical elements supporting light in the range between 800 and 1000 nm, especially 850 and 950 nm. An optical element refers to an element that exerts its functions by absorbing light of specific wavelengths. The present cyanine compound can suitably be used for near-infrared-ray absorbing materials for optical filters and laser-weldable resin compositions, as described above, and also as coloring agents for such applications as optical recording materials, optical filters for CCDs and CMOSs, dye sensitized solar cells, photoelectrochemical cells, nonlinear optical devices, electrochromic displays, holograms, organic semiconductors, organic ELs, silver halide photographic materials, sensitizers, printing ink, inkjets, electrophotographic color toners, cosmetic materials, and plastics, and also as protein dyeing agents and luminescent dyes for detecting substances.

Concrete examples of the cyanine compound of the invention include cyanine compounds containing the cation moiety (Compounds Nos. 1 to 60) given as examples in the description on the cyanine compounds usable in the near-infrared-ray absorbing material described above.

EXAMPLES

The present invention will be described in further detail below according to Examples and Comparative Examples. The invention, however, is not to be limited by the following Examples etc.

In Examples 1-1 to 1-9, cyanine compounds of the present invention, each containing one of Compounds Nos. 2, 3, 4, and 6 as the cation, were produced. In Examples 1-10 to 1-12, cyanine compounds relating to the invention, each containing an ion represented by the general formula (III) as the anion, were produced. Comparative Examples 1-1 to 1-4 show comparative cyanine compounds.

In Example 2 and Comparative Example 2, near-infrared-ray absorbing materials each containing one of the cyanine compounds of Examples 1-1 to 1-11 and Comparative Examples 1-1 to 1-4 were produced and were used to form respective evaluation films, whose absorption spectra etc. were measured. Further, in Evaluation Examples 1 and 2, the light resistance and heat resistance were evaluated for the evaluation films prepared in Example 2 and Comparative Example 2.

Example 1-1

Production of Tetrafluoroborate Salt of Compound No. 2

To 33 g of methanol were dissolved 3.41 g (8.4 mmol) of 3,3-dibenzyl-1,2-dimethyl-3H-indolium bromide and 1.24 g (4 mmol) of phenyl-(7-phenylaminohepta-2,4,6-trienylidene)ammonium chloride, and then, 0.93 g (9.2 mmol) of triethylamine was added thereto while stirring at room temperature. Then, 8.17 g (80 mmol) of acetic anhydride was dropped thereto while stirring at room temperature, and the mixture was heated under reflux for 2 hours. The mixture was cooled to room temperature, and then a solution of 0.66 g (6 mmol) of sodium tetrafluoroborate dissolved in 3.3 g of deionized water was dropped thereto. The precipitate was filtered off, recrystallized with chloroform/2-propanol, and was dried under reduced pressure at 100° C. for 2 hours, to give 0.7 g of an ocherous solid (yield: 21%).

Example 1-2

Production of Bis(Trifluoromethane Sulfone)Imide Salt of Compound No. 2

To 30.6 g of methanol were dissolved 2.56 g (6.3 mmol) of 3,3-dibenzyl-1,2-dimethyl-3H-indolium bromide and 0.93 g (3 mmol) of phenyl-(7-phenylaminohepta-2,4,6-trienylidene)ammonium chloride, and then, 0.7 g (6.9 mmol) of triethylamine was added thereto while stirring at room temperature. Then, 6.1 g (60 mmol) of acetic anhydride was dropped thereto while stirring at room temperature, and the mixture was heated under reflux for 2 hours. The mixture was cooled to room temperature, and then a solution of 1.44 g (4.5 mmol) of potassium bis(trifluoromethane sulfone)imide dissolved in 7 g of deionized water was dropped thereto. The precipitate was dispersed in methanol at room temperature for 1 hour, and the obtained solid was dried under reduced pressure at 100° C. for 2 hours, to give 2.06 g of a green solid (yield: 67%).

Example 1-3

Production of Tetrafluoroborate Salt of Compound No. 3

To 25 g of methanol were dissolved 2.4 g (6.3 mmol) of 3-benzyl-1,2,3-trimethyl-3H-benz[e]indolium bromide and 0.93 g (3 mmol) of phenyl-(7-phenylaminohepta-2,4,6-trienylidene)ammonium chloride, and then, 0.7 g (6.9 mmol) of triethylamine was added thereto while stirring at room temperature. Then, 6.13 g (60 mmol) of acetic anhydride was dropped thereto while stirring at room temperature, and the mixture was heated under reflux for 3 hours. The mixture was cooled to room temperature, and then a solution of 0.83 g (7.5 mmol) of sodium tetrafluoroborate dissolved in 8.3 g of deionized water was dropped thereto. The precipitate was filtered off, was recrystallized with acetone/2-propanol, and was dried under reduced pressure at 80° C. for 2 hours, to give 2.04 g of a dark-green solid (yield: 45%).

Example 1-4

Production of Bis(Trifluoromethane Sulfone)Imide Salt of Compound No. 3

To 25 g of methanol were dissolved 4.0 g (10.5 mmol) of 3-benzyl-1,2,3-trimethyl-3H-benz[e]indolium bromide and 1.55 g (5 mmol) of phenyl-(7-phenylaminohepta-2,4,6-trienylidene)ammonium chloride, and then, 1.16 g (11.5 mmol) of triethylamine was added thereto while stirring at room temperature. Then, 10.2 g (100 mmol) of acetic anhydride was dropped thereto while stirring at room temperature, and the mixture was heated under reflux for 3 hours. The mixture was cooled to room temperature, and then a solution of 2.4 g (7.5 mmol) of potassium bis(trifluoromethane sulfone)imide dissolved in 24 g of deionized water was dropped thereto. The precipitate was filtered off, recrystallized with chloroform/2-propanol, and was dried under reduced pressure at 80° C. for 2 hours, to give 3.09 g of a dark-green solid (yield: 64%).

Example 1-5

Production of Quencher (1-1) Salt of Compound No. 3

A solution of 1.28 g (1.65 mmol) of the tetrafluoroborate salt of Compound No. 2 obtained in Example 1-3 and 1.33 g (1.5 mmol) of a tetrabutylammonium salt of a quencher anion represented by the following formula (1-1) in 6 g of N,N'-dimethylformamide was heated, while being stirred, up to 40° C. The mixture was stirred at 40° C. for 1 hour, and then 60 g of methanol was dropped thereto at 40° C. The mixture was cooled to room temperature, and the precipitate was filtered off, recrystallized with acetone/methanol, and dried under reduced pressure at 80° C. for 3 hours, to give 0.89 g of a dark-green solid (yield: 46%).

[Chem. 15]

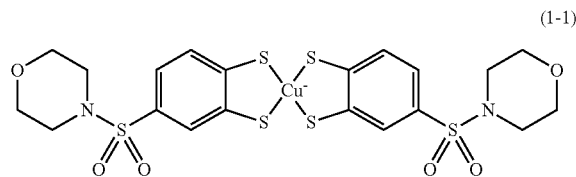

(1-1)

Example 1-6

Production of Tetrafluoroborate Salt of Compound No. 4

To 18.6 g of methanol were dissolved 1.58 g (4.2 mmol) of 3,3-dibenzyl-1-methyl-2-methylene-2,3-dihydro-1H-benz[e]indole and 0.62 g (2 mmol) of phenyl-(7-phenylamino-hepta-2,4,6-trienylidene)ammonium chloride, and then, 0.47 g (4.6 mmol) of triethylamine was added thereto while stirring at room temperature. Then, 4.1 g (40 mmol) of acetic anhydride was dropped thereto while stirring at room temperature, and the mixture was heated under reflux for 3 hours. The mixture was cooled to room temperature, and then a solution of 0.33 g (3 mmol) of sodium tetrafluoroborate dissolved in 10 g of deionized water was dropped thereto. The precipitate was filtered off, recrystallized with acetone/2-propanol, and was dried under reduced pressure at 80° C. for 3 hours, to give 0.96 g of a black solid (yield: 52%).

Example 1-7

Production of Bis(Trifluoromethane Sulfone)Imide Salt of Compound No. 4

To 18.6 g of methanol were dissolved 1.58 g (4.2 mmol) of 3,3-dibenzyl-1-methyl-2-methylene-2,3-dihydro-1H-benz[e]indole and 0.62 g (2 mmol) of phenyl-(7-phenylaminohepta-2,4,6-trienylidene)ammonium chloride, and then, 0.47 g (4.6 mmol) of triethylamine was added thereto while stirring at room temperature. Then, 4.1 g (40 mmol) of acetic anhydride was dropped thereto while stirring at room temperature, and the mixture was heated under reflux for 3 hours. The mixture was cooled to room temperature, and then a solution of 0.96 g (3 mmol) of potassium bis(trifluoromethane sulfone)imide dissolved in 10 g of deionized water was dropped thereto. The precipitate was filtered off, recrystallized with chloroform/2-propanol, and was dried under reduced pressure at 80° C. for 3 hours, to give 1.1 g of an ocherous solid (yield: 49%).

Example 1-8

Production of Quencher (1-1) Salt of Compound No. 4

To 14.85 g of N,N'-dimethylformamide were added 1.02 g (1.1 mmol) of the tetrafluoroborate salt of Compound No. 4 obtained in Example 1-6 and 0.88 g (1.0 mmol) of a tetrabutylammonium salt of the quencher anion represented by the formula (1-1), and the mixture was stirred and heated up to 60° C. After stirring the mixture at 60° C. for 1 hour, 22.27 g of methanol was dropped thereto at 60° C. The mixture was cooled to room temperature, and the precipitate was filtered off, recrystallized with N,N'-dimethylformamide/methanol, and dried under reduced pressure at 100° C. for 3 hours, to give 0.79 g of a dark-green solid (yield: 53%).

Example 1-9

Production of Tetrafluoroborate Salt of Compound No. 6

To 10 g of methanol were dissolved 1.02 g (2.1 mmol) of 3,3-dibenzyl-2-methyl-1-propyl-3H-benz[e]indolium bromide and 0.31 g (1 mmol) of phenyl-(7-phenylaminohepta-2,4,6-trienylidene)ammonium chloride, and then, 0.23 g (2.3 mmol) of triethylamine was added thereto while stirring at room temperature. Then, 2.04 g (20 mmol) of acetic anhydride was dropped thereto while stirring at room temperature, and the mixture was heated under reflux for 5 hours. The mixture was cooled to room temperature, and then a mixed solution of 0.27 g (2.5 mmol) of sodium tetrafluoroborate dissolved in 10 g of deionized water and 10 g of 2-propanol was dropped thereto. The precipitate was filtered off, recrystallized with acetone/2-propanol, and was dried under reduced pressure at 80° C. for 2 hours, to give 0.26 g of a dark-green solid (yield: 27%).

Analyses of the compounds obtained in Examples 1-1 to 1-9 showed that they were the respective target compounds. The analysis results of $^1$H-NMR are shown in Table 1.

TABLE 1

|  | Cation | Anion | $^1$HNMR/ppm(CDCl$_3$) |
|---|---|---|---|
| Example 1-1 | Compound No. 2 | BF$_4^-$ | 2.96(s, 6H), 3.51(d, 4H), 3.61(d, 4H), 6.06(d, 2H), 6.55(dd, 1H), 6.56(d, 2H), 6.58(dd, 2H), 6.63(d, 8H), 6.93(dd, 8H), 6.97(dd, 4H), 7.15(dd, 4H), 7.36(d, 2H), 7.52-7.62(m, 2H), 7.96(dd, 2H) |
| Example 1-2 | Compound No. 2 | (CF$_3$SO$_2$)$_2$N$^-$ | 2.99(s, 6H), 3.56(d, 4H), 3.66(d, 4H), 6.07(d, 2H), 6.61(dd, 1H), 6.62(d, 2H), 6.65(dd, 2H), 6.69(d, 8H), 6.99(dd, 8H), 7.04(dd, 4H), 7.22(dd, 4H), 7.43(d, 2H), 7.61-7.71(m, 2H), 8.02(dd, 2H) |
| Example 1-3 | Compound No. 3 | BF$_4^-$ | 2.14(s, 6H), 3.33(s, 6H), 3.61(d, 2H), 3.92(d, 2H), 6.19(d, 2H), 6.40(d, 4H), 6.56(dd, 1H), 6.63(dd, 2H), 6.81(dd, 4H), 6.93(dd, 2H), 7.05(d, 2H), 7.48(dd, 2H), 7.51(dd, 2H), 7.67(dd, 2H), 7.81(d, 2H), 7.91(d, 2H), 7.93(dd, 2H), 8.26(d, 2H) |

TABLE 1-continued

| | Cation | Anion | $^1$HNMR/ppm(CDCl$_3$) |
|---|---|---|---|
| Example 1-4 | Compound No. 3 | (CF$_3$SO$_2$)$_2$N$^-$ | 2.14(s, 6H), 3.30(s, 6H), 3.59(d, 2H), 3.93(d, 2H), 6.13(d, 2H), 6.39(d, 4H), 6.57(dd, 1H), 6.62(dd, 2H), 6.82(dd, 4H), 6.94(dd, 2H), 7.04(d, 2H), 7.44-7.52(m, 2H), 7.49(dd, 2H), 7.69(dd, 2H), 7.83(d, 2H), 7.92(dd, 2H), 7.93(d, 2H), 8.27(d, 2H) |
| Example 1-5 | Compound No. 3 | Quencher (1-1) | 2.15(s, 6H), 2.93(ddd, 8H), 3.24(s, 6H), 3.56(dd, 2H), 3.68(ddd, 8H), 3.91(d, 2H), 6.09(dd, 2H), 6.39(dd, 4H), 6.40(dd, 2H), 6.52(dd, 1H), 6.82(ddd, 4H), 6.95(dd, 2H), 6.98(d, 2H), 7.06(d, 2H), 7.21-7.30(m, 4H), 7.32(dd, 2H), 7.49(dd, 2H), 7.68(dd, 2H), 7.79(dd, 2H), 7.80(d, 2H), 7.92(d, 2H), 8.24(d, 2H) |
| Example 1-6 | Compound No. 4 | BF$_4$$^-$ | 3.10(s, 6H), 3.83(d, 4H), 4.18(d, 4H), 6.21(d, 2H), 6.51(d, 8H), 6.64-6.75(m, 3H), 6.82(d, 2H), 6.83(dd, 8H), 6.93(dd, 4H), 7.53(dd, 2H), 7.60-7.70(m, 2H), 7.75(d, 2H), 7.77(dd, 2H), 7.93(d, 2H), 8.14(dd, 2H), 8.50(d, 2H) |
| Example 1-7 | Compound No. 4 | (CF$_3$SO$_2$)$_2$N$^-$ | 3.06(s, 6H), 3.81(d, 4H), 4.18(d, 4H), 6.16(d, 2H), 6.51(d, 8H), 6.64-6.74(m, 3H), 6.82(d, 2H), 6.83(dd, 8H), 6.94(dd, 4H), 7.54(dd, 2H), 7.60-7.70(m, 2H), 7.76(d, 2H), 7.79(dd, 2H), 7.94(d, 2H), 8.14(dd, 2H), 8.50(d, 2H) |
| Example 1-8 | Compound No. 4 | Quencher (1-1) | 2.89(ddd, 8H), 3.02(s, 6H), 3.65(ddd, 8H), 3.83(d, 4H), 4.19(d, 4H), 6.16(d, 2H), 6.51(d, 8H), 6.57-6.70(m, 3H), 6.80(d, 2H), 6.82(dd, 8H), 6.92(dd, 4H), 7.09(dd, 2H), 7.27(dd, 2H), 7.38(dd, 2H), 7.41-7.52(m, 2H), 7.54(dd, 2H), 7.75(d, 2H), 7.80(dd, 2H), 7.94(d, 2H), 8.01-8.11(m, 2H), 8.50(d, 2H) |
| Example 1-9 | Compound No. 6 | BF$_4$$^-$ | 0.54(t, 6H), 1.14(tq, 4H), 3.47(t, 4H), 3.88(d, 4H), 4.24(d, 4H), 6.14(d, 2H), 6.49(d, 8H), 6.66-6.76(m, 3H), 6.81(d, 2H), 6.82(dd, 8H), 6.92(dd, 4H), 7.54(dd, 2H), 7.66-7.74(m, 2H), 7.77(d, 2H), 7.79(dd, 2H), 7.95(d, 2H), 8.17-8.28(m, 2H), 8.55(d, 2H) |

Also, the compounds obtained in Examples 1-1 to 1-9 were subjected to UV-Visible absorption spectra measurement, decomposition point measurement, and solubility measurement, according to the procedures described below. The results are shown in Table 2.

The UV-Visible absorption spectra measurement was conducted by preparing a chloroform solution of each compound to be tested, and employing a UV-Vis-NIR spectrophotometer ("V-570"; product from JASCO Corporation). The decomposition point measurement was conducted using a thermogravimetry differential thermal analyzer ("TG/DTA 6200"; product from Seiko Instruments Inc.), to find the temperature at which the mass started to decrease in differential thermal analysis at a temperature-rise rate of 10° C./minute.

The solubility measurement was conducted as follows: the compound to be tested was weighed; methyl ethyl ketone (MEK) was slowly added thereto; when the solute completely dissolved, the solution was weighed; and the concentration of the test compound in the solution was determined by calculation.

Examples 1-10 to 1-12

According to the procedures of Examples 1-1 to 1-9, a bis(trifluoromethane sulfone)imide salt of Compound No. 61 (Example 1-10), a bis(trifluoromethane sulfone)imide salt of Compound No. 64 (Example 1-11), and a bis(trifluoromethane sulfone)imide salt of Compound No. 105 (Example 1-12) were synthesized.

The cyanine compounds obtained in Examples 1-10 to 1-12 were subjected to UV-Vis absorption spectra measurement, decomposition point measurement, and solubility measurement, as described above. The results are shown in Table 2.

Comparative Examples 1-1 to 1-4

Compounds having one of the Compounds Nos. 61, 64, and 105 as the cation and either one of BF$_4$$^-$ or the quencher (1-1) as the anion were employed as comparative cyanine compounds (see Table 2). These comparative compounds were subjected to UV-Vis absorption spectra measurement, decomposition point measurement, and solubility measurement, as in Example 1, The results are shown in Table 2.

TABLE 2

| | Test Compounds | | UV-Vis Absorption Spectra | | Decomposition | Solubility |
|---|---|---|---|---|---|---|
| | Cation | Anion | λmax/nm | ε/10$^5$ | Point/° C. | (MEK)/wt % |
| Example 1-1 | Compound No. 2 | BF$_4$$^-$ | 889 | 2.51 | 238.3 | 0.16 |
| Example 1-2 | Compound No. 2 | (CF$_3$SO$_2$)$_2$N$^-$ | 894 | 3.12 | 248.6 | 2.34 |
| Example 1-3 | Compound No. 3 | BF$_4$$^-$ | 920 | 2.41 | 180.5 | 0.97 |
| Example 1-4 | Compound No. 3 | (CF$_3$SO$_2$)$_2$N$^-$ | 925 | 2.68 | 255.8 | 0.98 |
| Example 1-5 | Compound No. 3 | Quencher (1-1) | 928 | 3.17 | 249.1 | 0.39 |

TABLE 2-continued

|  | Test Compounds | | UV-Vis Absorption Spectra | | Decomposition Point/° C. | Solubility (MEK)/wt % |
|---|---|---|---|---|---|---|
|  | Cation | Anion | λmax/nm | ε/10⁵ | | |
| Example 1-6 | Compound No. 4 | BF₄⁻ | 936 | 2.28 | 192.6 | 1.62 |
| Example 1-7 | Compound No. 4 | (CF₃SO₂)₂N⁻ | 939 | 2.95 | 266.5 | 3.71 |
| Example 1-8 | Compound No. 4 | Quencher (1-1) | 941 | 2.94 | 258.8 | 3.69 |
| Example 1-9 | Compound No. 6 | BF₄⁻ | 944 | 2.47 | 193.8 | 1.36 |
| Example 1-10 | Compound No. 61 | (CF₃SO₂)₂N⁻ | 866 | 2.43 | 238.4 | 0.73 |
| Example 1-11 | Compound No. 64 | (CF₃SO₂)₂N⁻ | 937 | 3.00 | 280.7 | 1.46 |
| Example 1-12 | Compound No. 105 | (CF₃SO₂)₂N⁻ | 937 | 2.48 | 291.5 | 1.13 |
| Comparative Example 1-1 | Compound No. 61 | BF₄⁻ | 866 | 1.94 | 196.6 | 0.21 |
| Comparative Example 1-2 | Compound No. 64 | BF₄⁻ | 934 | 2.57 | 257.7 | 0.43 |
| Comparative Example 1-3 | Compound No. 64 | Quencher (1-1) | 937 | 2.68 | 198.7 | 0.20 |
| Comparative Example 1-4 | Compound No. 105 | Quencher (1-1) | 942 | 2.09 | 261.3 | 0.28 |

Example 2 and Comparative Example 2

Near-infrared-ray absorbing materials, in solution form, were prepared according to the procedure described below using the respective compounds obtained in Examples 1-1 to 1-11 and Comparative Examples 1-1 to 1-4 as the test compounds. Further, each near-infrared-ray absorbing material was used to prepare a resin composition, and each resin composition was used to prepare an evaluation film.

Preparation of Near-Infrared-Ray Absorbing Material and Resin Composition:

Each test compound was dissolved in methyl ethyl ketone so that the concentration was 0.5% by mass, thus preparing each near-infrared-ray absorbing material in solution form. With 0.4 g of each near-infrared-ray absorbing material was mixed 3.0 g of a toluene solution containing polymethyl methacrylate (also referred to hereinafter as PMMA) at a concentration of 25% by mass, and the mixture was subjected to ultrasonic irradiation for 15 minutes, thus preparing a resin composition (coating fluid).

Preparation of Evaluation Film:

Using a bar coater #30, each coating fluid prepared as above was coated on a 188-μm-thick polyethylene terephthalate film pre-treated for easy adhesion, and dried at 100° C. for 10 minutes, thus forming, on the polyethylene terephthalate film, an evaluation film (7 to 8 μm thick) containing the respective test compound.

The absorption spectra were measured for each of the prepared evaluation films using a UV-Vis-NIR spectrophotometer ("V-570"; product from JASCO Corporation). The results are shown in Table 3.

TABLE 3

|  | Test Compounds | | λmax/nm | Half-Width/nm |
|---|---|---|---|---|
|  | Cation | Anion | | |
| Example 2-1 | Compound No. 2 | BF₄⁻ | 882 | 141 |
| Example 2-2 | Compound No. 2 | (CF₃SO₂)₂N⁻ | 889 | 96 |
| Example 2-3 | Compound No. 3 | BF₄⁻ | 913 | 164 |
| Example 2-4 | Compound No. 3 | (CF₃SO₂)₂N⁻ | 922 | 103 |
| Example 2-5 | Compound No. 3 | Quencher (1-1) | 926 | 92 |
| Example 2-6 | Compound No. 4 | BF₄⁻ | 928 | 133 |
| Example 2-7 | Compound No. 4 | (CF₃SO₂)₂N⁻ | 936 | 95 |
| Example 2-8 | Compound No. 4 | Quencher (1-1) | 939 | 88 |
| Example 2-9 | Compound No. 6 | BF₄⁻ | 937 | 108 |
| Example 2-10 | Compound No. 61 | (CF₃SO₂)₂N⁻ | 864 | 111 |
| Example 2-11 | Compound No. 64 | (CF₃SO₂)₂N⁻ | 922 | 143 |
| Comparative Example 2-1 | Compound No. 61 | BF₄⁻ | 858 | 170 |
| Comparative Example 2-2 | Compound No. 64 | BF₄⁻ | 912 | 175 |
| Comparative Example 2-3 | Compound No. 64 | Quencher (1-1) | 930 | 186 |
| Comparative Example 2-4 | Compound No. 105 | Quencher (1-1) | 913 | 164 |

Table 3 shows that, when comparing the samples having the same anions, the evaluation films containing the cyanine compounds of the invention have narrow half-widths and exhibit sharp peaks in the wavelength range between 800 and 1000 nm, whereas the evaluation films containing the comparative compounds have wide peak with half-widths spanning a relatively wide band, although their peaks were in the wavelength range between 800 and 1000 nm. Further, the evaluation films containing the cyanine compounds relating to the invention wherein the anion is an ion represented by the general formula (III) also had narrow half-widths. These results show that the near-infrared-ray absorbing materials of the invention are useful as materials for absorbing light of specific wavelengths more selectively.

Evaluation Example 1

Light Resistance Evaluation

The evaluation films obtained in Example 2 and Comparative Example 2 were treated in a fade meter ("Table Sun TS-2"; product of Suga Test Instruments Co., Ltd.) for 12 hours, and then their absorption spectra were measured as in Example 2. Considering the transmittance at the maximum absorption wavelength before treatment as 100%, the decrease in transmittance at the maximum absorption wavelength after treatment was found by calculation as the residual rate of colorants. The results are shown in Table 4.

TABLE 4

|  | Test Compounds | | Light Resistance |
|---|---|---|---|
|  | Cation | Anion | (12 h)/% |
| Example 2-1 | Compound No. 2 | $BF_4^-$ | 63.5 |
| Example 2-2 | Compound No. 2 | $(CF_3SO_2)_2N^-$ | 60.1 |
| Example 2-3 | Compound No. 3 | $BF_4^-$ | 54.7 |
| Example 2-5 | Compound No. 3 | Quencher (1-1) | 99.1 |
| Example 2-6 | Compound No. 4 | $BF_4^-$ | 63.2 |
| Example 2-7 | Compound No. 4 | $(CF_3SO_2)_2N^-$ | 72.4 |
| Example 2-8 | Compound No. 4 | Quencher (1-1) | 99.5 |
| Example 2-9 | Compound No. 6 | $BF_4^-$ | 80.5 |
| Example 2-10 | Compound No. 61 | $(CF_3SO_2)_2N^-$ | 31.5 |
| Example 2-11 | Compound No. 64 | $(CF_3SO_2)_2N^-$ | 20.6 |
| Comparative Example 2-1 | Compound No. 61 | $BF_4^-$ | 42.1 |
| Comparative Example 2-2 | Compound No. 64 | $BF_4^-$ | 24.3 |
| Comparative Example 2-4 | Compound No. 105 | Quencher (1-1) | 91.4 |

The results show that, when comparing the Examples and the Comparative Examples having the same anions, the cyanine compounds of the invention all exhibit excellent light resistance, whereas the conventional cyanine compounds are inferior thereto in light resistance. Further, it is shown that the cyanine compounds relating to the invention in which $R^1$ is a group represented by the general formula (II) or (II') have especially good light resistance.

Evaluation Example 2

The evaluation films obtained in Example 2 and Comparative Example 2 were heated in a constant temperature bath at 80° C., and their absorption spectra were measured, as in Example 2, 100 hours and 300 hours after having started heating. Considering the transmittance at the maximum absorption wavelength before starting heating as 100%, the decrease in transmittance at the maximum absorption wavelength after heating was found by calculation as the residual rate of colorants. The results are shown in Table 5.

TABLE 5

|  | Test Compounds | | Heat Resistance/% | |
|---|---|---|---|---|
|  | Cation | Anion | 100 h | 300 h |
| Example 2-1 | Compound No. 2 | $BF_4^-$ | 98.9 | 96.8 |
| Example 2-2 | Compound No. 2 | $(CF_3SO_2)_2N^-$ | 99.6 | 99.6 |
| Example 2-3 | Compound No. 3 | $BF_4^-$ | 97.7 | 96.0 |
| Example 2-5 | Compound No. 3 | Quencher (1-1) | 99.0 | 98.2 |
| Example 2-6 | Compound No. 4 | $BF_4^-$ | 98.6 | 97.3 |
| Example 2-7 | Compound No. 4 | $(CF_3SO_2)_2N^-$ | 99.2 | 98.3 |
| Example 2-8 | Compound No. 4 | Quencher (1-1) | 99.5 | 98.7 |
| Example 2-9 | Compound No. 6 | $BF_4^-$ | 99.5 | 98.8 |
| Example 2-10 | Compound No. 61 | $(CF_3SO_2)_2N^-$ | 99.1 | 98.7 |
| Example 2-11 | Compound No. 64 | $(CF_3SO_2)_2N^-$ | 97.8 | 94.1 |
| Comparative Example 2-1 | Compound No. 61 | $BF_4^-$ | 95.1 | 91.1 |
| Comparative Example 2-2 | Compound No. 64 | $BF_4^-$ | 95.5 | 91.0 |
| Comparative Example 2-4 | Compound No. 105 | Quencher (1-1) | 94.9 | 93.7 |

The results show that, when comparing the Examples and the Comparative Examples having the same anions, the cyanine compounds of the invention all exhibit excellent heat resistance, whereas the conventional cyanine compounds are inferior thereto in heat resistance. Further, it is shown that the cyanine compounds relating to the invention in which the anion is an ion represented by the general formula (III) also have excellent heat resistance.

The results of the above Examples and Evaluation Examples show that the near-infrared-ray absorbing materials of the present invention are suitable for optical filters and laser-weldable resin compositions and that the cyanine compounds of the present invention have excellent properties, and especially good light resistance.

The invention claimed is:
1. A near-infrared-ray absorbing material containing at least one cyanine compound represented by general formula (I) shown below:

[Chem. 1]

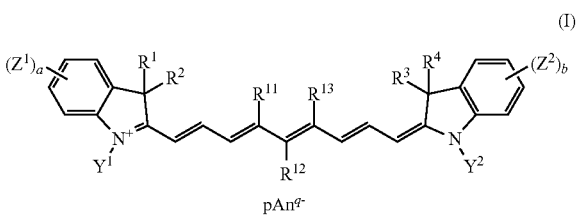

(I)

wherein: $R^1$, $R^2$, $R^3$, $R^4$, $Y^1$, and $Y^2$ each independently represent a hydrogen atom, a group represented by general formula (II) or general formula (II') shown below, a $C_{1-20}$ alkyl group, a $C_{6-30}$ aryl group, or a $C_{7-30}$ arylalkyl group, an alkylene moiety of the alkyl group or the arylalkyl group being optionally interrupted by —O— or —S—; $R^1$ and $R^2$, as well as $R^3$ and $R^4$, may independently be connected with each other to form a 3- to 6-membered alicyclic group;

$An^{q-}$ represents a q-valent anion; q is an integer of 1 or 2; p represents a coefficient for keeping the electrical charge neutral;

with the proviso that at least either $R^1$ is a group represented by the general formula (II) or (II'), or the anion represented by $An^{q-}$ is an ion represented by general formula (III) shown below;

$R^{11}$, $R^{12}$, and $R^{13}$ each independently represent a hydrogen atom, a hydroxyl group, a halogen atom, a cyano group, a diphenylamino group, a $C_{1-20}$ alkyl group, a $C_{6-30}$ aryl group, or a $C_{7-30}$ arylalkyl group, an alkylene moiety of the alkyl group or the arylalkyl group being optionally interrupted by —O— or —S—; $R^{11}$ and $R^{13}$ may be connected to each other to form a 4- to 8-membered cycloalkene ring, a methylene moiety of the formed cycloalkene ring being optionally substituted by a hydroxyl group, a halogen atom, a cyano group, a $C_{6-30}$ aryl group, a diphenylamino group, a $C_{1-8}$ alkyl group, or a $C_{1-8}$ alkoxy group;

$Z^1$ and $Z^2$ each independently represent a $C_{1-10}$ alkyl group, a $C_{6-20}$ aryl group, a $C_{7-20}$ arylalkyl group, a nitro group, a cyano group, a hydroxyl group, a carboxyl group, or a halogen atom, or a plurality of the $Z^1$ groups, or a plurality of the $Z^2$ groups, may be bonded together to form a ring structure; a hydrogen atom in $Z^1$ and $Z^2$ may optionally be substituted by a nitro group, a cyano group, a hydroxyl group, a carboxyl group, or a halogen atom; a methylene group in $Z^1$ and $Z^2$ may optionally be interrupted by —O—, —CO—, —OCO—, or —COO—; and a and b each independently represent an integer of 0 to 4;

[Chem. 2]

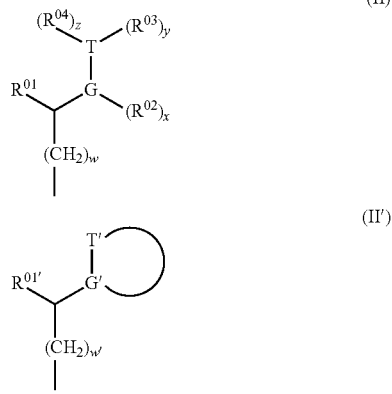

(II)

(II')

in the above general formula (II): the bond between G and T is a double bond, a conjugated double bond, or a triple bond; G represents a carbon atom; T represents a carbon atom, an oxygen atom, or a nitrogen atom; w represents a number from 0 to 4; x, y, and z each represent 0 or 1 (if T is an oxygen atom, then y and z are 0; if T is a nitrogen atom, then y+z is 0 or 1); $R^{01}$, $R^{02}$, $R^{03}$, and $R^{04}$ each independently represent a hydrogen atom, a hydroxyl group, a nitro group, a cyano group, a halogen atom, or a $C_{1-4}$ alkyl group that may optionally have a substituent, a methylene group in the alkyl group being optionally replaced by —O— or —CO—; and $R^{01}$ and $R^{04}$ may be bonded to form a cycloalkene ring or a heterocycle;

in the above general formula (II'): the bond between G' and T' is a double bond or a conjugated double bond; G' represents a carbon atom; T' represents a carbon atom or a nitrogen atom; the ring containing G' and T' represents a 5-membered ring that may contain a hetero atom, a 6-membered ring that may contain a hetero atom, a naphthalene ring, a quinoline ring, an isoquinoline ring, an anthracene ring, or an anthraquinone ring; the ring containing G' and T' may optionally be substituted by a halogen atom, a hydroxyl group, a nitro group, a cyano group, a $C_{1-4}$ alkyl group, or a $C_{1-4}$ alkoxy group; w' represents a number from 0 to 4; and $R^{01'}$ represents a hydrogen atom, a hydroxyl group, a nitro group, a cyano group, a halogen atom, or a $C_{1-4}$ alkyl group that may optionally have a substituent, a methylene group in the alkyl group being optionally replaced by —O— or —CO—;

[Chem. 3]

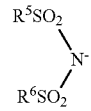

(III)

wherein, $R^5$ and $R^6$ each independently represent a halogen-substituted $C_{1-8}$ alkyl group.

2. The near-infrared-ray absorbing material according to claim 1, wherein $R^1$ in the general formula (I) is a group represented by the general formula (II) or the general formula (II').

3. The near-infrared-ray absorbing material according to claim 1, wherein $R^1$ in the general formula (I) is a group represented by the general formula (II').

4. The near-infrared-ray absorbing material according to claim 1, wherein $R^3$ in the general formula (I) is a group represented by the general formula (II').

5. The near-infrared-ray absorbing material according to claim 1, wherein all of $R^1$ to $R^4$ in the general formula (I) are groups represented by the general formula (II').

6. The near-infrared-ray absorbing material according to claim 1, wherein the group represented by the general formula (II') is a group represented by general formula (IV) shown below:

[Chem. 4]

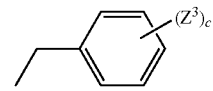

(IV)

wherein, $Z^3$ represents a halogen atom, a hydroxyl group, a nitro group, a cyano group, a $C_{1-4}$ alkyl group that may optionally be substituted by a halogen atom, or a $C_{1-4}$ alkoxy group that may optionally be substituted by a halogen atom; and c represents a number of 0 to 5.

7. The near-infrared-ray absorbing material according to claim 1, wherein the anion represented by $An^{q-}$ in the general formula (I) is an ion represented by the general formula (III).

8. A film-forming composition containing the near-infrared-ray absorbing material according to claim 1.

9. An optical filter made using the film-forming composition according to claim 8.

10. The optical filter according to claim 9, being used for an image display device.

11. The optical filter according to claim 10, wherein the image display device is a plasma display.

12. A resin composition for laser welding, containing the near-infrared-ray absorbing material according to claim 1.

13. A cyanine compound represented by general formula (I) shown below:

[Chem. 5]

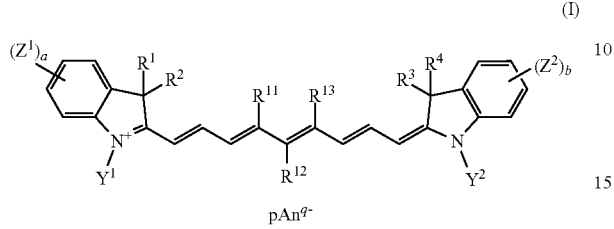
(I)

wherein: $R^1$ is a group represented by general formula (II) or (II') shown below;

$R^2$, $R^3$, $R^4$, $Y^1$, and $Y^2$ each independently represent a hydrogen atom, a group represented by the general formula (II) or the general formula (II'), a $C_{1-20}$ alkyl group, a $C_{6-30}$ aryl group, or a $C_{7-30}$ arylalkyl group, an alkylene moiety of the alkyl group or the arylalkyl group being optionally interrupted by —O— or —S—; $R^3$ and $R^4$ may be connected with each other to form a 3- to 6-membered alicyclic group;

$An^{q-}$ represents a q-valent anion; q is an integer of 1 or 2; p represents a coefficient for keeping the electrical charge neutral;

$R^{11}$, $R^{12}$, and $R^{13}$ each independently represent a hydrogen atom, a hydroxyl group, a halogen atom, a cyano group, a diphenylamino group, a $C_{1-20}$ alkyl group, a $C_{6-30}$ aryl group, or a $C_{7-30}$ arylalkyl group, an alkylene moiety of the alkyl group or the arylalkyl group being optionally interrupted by —O— or —S—; $R^{11}$ and $R^{13}$ may be connected to each other to form a 4- to 8-membered cycloalkene ring, a methylene moiety of the formed cycloalkene ring being optionally substituted by a hydroxyl group, a halogen atom, a cyano group, a $C_{6-30}$ aryl group, a diphenylamino group, a $C_{1-8}$ alkyl group, or a $C_{1-8}$ alkoxy group;

$Z^1$ and $Z^2$ each independently represent a $C_{1-10}$ alkyl group, a $C_{6-20}$ aryl group, a $C_{7-20}$ arylalkyl group, a nitro group, a cyano group, a hydroxyl group, a carboxyl group, or a halogen atom, or a plurality of the $Z^1$ groups, or a plurality of the $Z^2$ groups, may be bonded together to form a ring structure; a hydrogen atom in $Z^1$ and $Z^2$ may optionally be substituted by a nitro group, a cyano group, a hydroxyl group, a carboxyl group, or a halogen atom; a methylene group in $Z^1$ and $Z^2$ may optionally be interrupted by —O—, —CO—, —OCO—, or —COO—; and a and b each independently represent an integer of 0 to 4;

[Chem. 6]

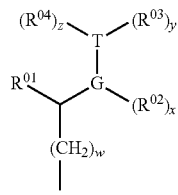
(II)

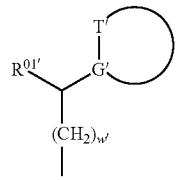
(II')

in the above general formula (II): the bond between G and T is a double bond, a conjugated double bond, or a triple bond; G represents a carbon atom; T represents a carbon atom, an oxygen atom, or a nitrogen atom; w represents a number from 0 to 4; x, y, and z each represent 0 or 1 (if T is an oxygen atom, then y and z are 0; if T is a nitrogen atom, then y+z is 0 or 1) ; $R^{01}$, $R^{02}$, $R^{03}$, and $R^{04}$ each independently represent a hydrogen atom, a hydroxyl group, a nitro group, a cyano group, a halogen atom, or a $C_{1-4}$ alkyl group that may optionally have a substituent, a methylene group in the alkyl group being optionally replaced by —O— or —CO—; and $R^{01}$ and $R^{04}$ may be bonded to form a cycloalkene ring or a heterocycle;

in the above general formula (II'): the bond between G' and T' is a double bond or a conjugated double bond; G' represents a carbon atom; T' represents a carbon atom or a nitrogen atom; the ring containing G' and T' represents a 5-membered ring that may contain a hetero atom, a 6-membered ring that may contain a hetero atom, a naphthalene ring, a quinoline ring, an isoquinoline ring, an anthracene ring, or an anthraquinone ring; the ring containing G' and T' may optionally be substituted by a halogen atom, a hydroxyl group, a nitro group, a cyano group, a $C_{1-4}$ alkyl group, or a $C_{1-4}$ alkoxy group; w' represents a number from 0 to 4; and $R^{01'}$ represents a hydrogen atom, a hydroxyl group, a nitro group, a cyano group, a halogen atom, or a $C_{1-4}$ alkyl group that may optionally have a substituent, a methylene group in the alkyl group being optionally replaced by —O— or —CO—.

14. The cyanine compound according to claim 13, wherein $R^1$ in the general formula (I) is a group represented by the general formula (II').

15. The cyanine compound according to claim 13, wherein $R^3$ in the general formula (I) is a group represented by the general formula (II').

16. The cyanine compound according to claim 13, wherein all of $R^1$ to $R^4$ in the general formula (I) are groups represented by the general formula (II').

17. The cyanine compound according to claim 13, wherein the group represented by the general formula (II') is a group represented by general formula (IV) shown below:

[Chem. 7]

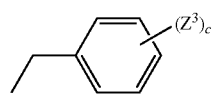
(IV)

wherein, $Z^3$ represents a halogen atom, a hydroxyl group, a nitro group, a cyano group, a $C_{1-4}$ alkyl group that may optionally be substituted by a halogen atom, or a $C_{1-4}$ alkoxy group that may optionally be substituted by a halogen atom; and c represents a number of 0 to 5.

18. The cyanine compound according to claim 13, wherein the anion represented by $An^{q-}$ in the general formula (I) is an ion represented by the general formula (III).

19. The near-infrared-ray absorbing material according to claim 2, wherein $R^3$ in the general formula (I) is a group represented by the general formula (II').

20. The near-infrared-ray absorbing material according to claim 3, wherein $R^3$ in the general formula (I) is a group represented by the general formula (II').

* * * * *